(12) United States Patent
Ljubimova et al.

(10) Patent No.: US 7,935,677 B2
(45) Date of Patent: May 3, 2011

(54) POLYMALIC ACID-BASED MULTI-FUNCTIONAL DRUG DELIVERY SYSTEM

(75) Inventors: Julia Y. Ljubimova, Studio City, CA (US); Keith L. Black, Los Angeles, CA (US); Eggehard Holler, Regensburg (DE)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 10/580,999

(22) PCT Filed: Dec. 3, 2004

(86) PCT No.: PCT/US2004/040660
§ 371 (c)(1),
(2), (4) Date: Mar. 12, 2007

(87) PCT Pub. No.: WO2005/155980
PCT Pub. Date: Jun. 23, 2005

(65) Prior Publication Data
US 2007/0259008 A1     Nov. 8, 2007

Related U.S. Application Data

(60) Provisional application No. 60/527,330, filed on Dec. 5, 2003.

(51) Int. Cl.
*C12N 15/11*     (2006.01)
*A61K 47/30*     (2006.01)
*A61K 9/00*      (2006.01)

(52) U.S. Cl. .................. 514/44; 424/400; 514/772.3

(58) Field of Classification Search .................. None
See application file for complete search history.

(56) References Cited

U.S. PATENT DOCUMENTS 6,472,512 B1 *  10/2002  LaFleur et al. ............. 530/388.2
7,056,532 B1 *   6/2006  Kabanov et al. ............ 424/486
2002/0155440 A1 10/2002  Black et al.

FOREIGN PATENT DOCUMENTS

WO      01/87239 A2    11/2001
WO      02/059610 A2    8/2002
WO    2005/028617 A2    3/2005
WO    2005/055980 A2    6/2005

OTHER PUBLICATIONS

Odian, G. (1991) Principles of Polymerization, Third Edition. John Wiley and Sons, Inc.*
Yu, et al. (2009) Targeted Delivery Systems for Oligonucleotide Therapeutics. The AAPS Journal, v.11(1):195-203.*
Bulmus et al. (Journal of Controlled Release 93 (Nov. 18, 2003) 105-120.*

Khazenzon, A.J. et al., Novel angiogenic targets for human glioma prevention and regulation of their expression, International Journal of Molecular Medicine, 2002, 10: Supplement 1, p. S41, XP008091390.
Ljubimova, J.Y. et al., A new multifunctional drug delivery system based on polymalic acid to inhibit angiogenesis and invasion of human gliomas in vitro and in vivo, European Journal of Cancer, Supplement, 2004, 2:8, p. 184, XP004640052.
Ljubimova, J.Y. et al., Development of an in vitro system to block the angiogenic target, laminin-8, in human gliomas, Proceedings of the American Association for Cancer Research Annual Meeting, Mar. 2002, vol. 43, p. 177, XP001536931.
Albini et al., A Rapid In Vitro Assay for Quantitating the Invasive Potential of Tumor Cells, Cancer Research, (Jun. 15, 1987), pp. 3239-3245, 47(12).
Andrews et al., Results of a Pilot Study Involving the Use of an Antisense Oligodeoxynucleotide Directed Against the Insulin-Like Growth Factor Type I Receptor in Malignant Astrocytomas, Journal of Clinical Oncology, (Apr. 15, 2001), pp. 2189-2200, 19(8).
Arora et al., c- Myc Antisense Limits Rat Liver Regeneration and Indicates Role for c-myc in Regulating Cytochrome P-450 3A Activity, Journal of Pharmacology and Experimental Therapeutics, (Mar. 2000), pp. 921-928, 292(3).
Astriab-Fisher et al., Antisense Inhibition of P-Glycoprotein Expression Using Peptide-Oligonucleotide Conjugates, Biochemical Pharmacology (Jul. 1, 2000), pp. 83-90, 60(1).
Belkin et al., Integrins As Receptors for Laminins, Microscopy Research and Technique, (Nov. 1, 2000), pp. 280-301, 51(3).

(Continued)

*Primary Examiner* — Janet L. Epps-Smith
(74) *Attorney, Agent, or Firm* — Lawson & Weitzen, LLP; Sonia K. Guteman; Marina Sigareva

(57) ABSTRACT

A structured drug system that is useful for delivering a drug payload to a specific tissue or cell type is disclosed. The system is based on purified polymalic acid. This polymer isolated from natural sources is biocompatible, biodegradable and of very low toxicity. The polymer is extremely water soluble and contains a large number of free carboxyl groups which can used to attach a number of different active molecules. In the examples disclosed N-hydroxysuccinimide esters of the carboxyl groups are used to attach such molecules. The active molecules include monoclonal antibodies to promote specific cellular uptake and specific pro-drugs such as antisense nucleic acids designed to modify the cellular metabolism of a target cell. The pro-drugs are advantageously linked by a somewhat labile bond so that they will be released under specific conditions. In addition, the system contains amide-linked valine to encourage membrane disruption under lysosomal conditions. Polyethylene glycol groups are attached to extend the drug system's circulation half-life. In addition, fluorescent reported groups can be readily included to aid in visualizing and confirming drug system targeting. The drug system can deliver treatments for a wide range of diseases and is specially advantageous for treatment of neoplasms.

18 Claims, 19 Drawing Sheets

OTHER PUBLICATIONS

Bello et al., Simultaneous Inhibition of Glioma Angiogenesis, Cell Proliferation, and Invasion by a Naturally Occurring Fragment of Human Metalloproteinase-2, Cancer Research, (Dec. 15, 2001), pp. 8730-8736, 61(24).

Boado et al., Antisense-Mediated Down-Regulation of the Human Huntingtin Gene, Journal of Pharmacology and Experimental Therapy, (Oct. 2000), pp. 239-243, 295(1).

Colognato et al., Form and Function: The Laminin Family of Heterotrimers, Developmental Dynamics, (Jun. 2000), pp. 213-234, 218(2).

De Diesbach et al., Identification, Purification and Partial Characterisation of an Oligonucleotide Receptor in Membranes of HepG2 Cells, Nucleic Acids Research, (Feb. 15, 2000), pp. 868-874, 28(4).

Dias et al., Antisense Oligonucleotides : Basic Concepts and Mechanisms, Molecular Cancer Therapy, (Mar. 2002), pp. 347-355, 1(5).

Fujiwara et al., Purification and Characterization of Human Laminin-8. Laminin-8 Stimulates Cell Adhesion and Migration Through a3β1 and a6p, Integrins, Journal of Biological Chemistry, (May 18, 2001), pp. 17550-17558, 276(20).

Gonzalez et al., Complex Interactions Between the Laminin a4 Subunit and Integrins Regulate Endothelial Cell Behavior In Vitro and Angiogenesis In Vivo, Proceedings of the National Academy of Sciences USA, (Dec. 10, 2002), pp. 16075-16080, 99(25).

Hayashi et al., Identification and Recombinant Production of Human Laminin a4 Subunit Splice Variants, Biochemical and Biophysical Research Communications, (Dec. 6, 2002), pp. 498-504, 299(3).

Herold-Mende et al., Clinical Impact and Functional Aspects of Tenascin-C Expression During Glioma Progression, International Journal of Cancer, (Mar. 20, 2002), pp. 362-369, 98(3).

Jansen et al., Chemosensitisation of Malignant Melanoma by BCL2 Antisense Therapy, Lancet, (Nov. 18, 2000), pp. 1728-1733, 356(9243).

Kachra et al., Expression of Matrix Metalloproteinases and Their Inhibitors in Human Brain Tumors, Clinical and Experimental Metastasis, (1999), pp. 555-566, 17(7).

Kleinman et al., Basement Membrane Complexes With Biological Activity, Biochemistry, (Jan. 28, 1986), pp. 312-318, 25(2).

Knott et al., Stimulation of Extracellular Matrix Components in the Normal Brain by Invading Glioma Cells, International Journal of Cancer, (Mar. 16, 1998), pp. 864-872, 75(6).

Komata et al., Combination Therapy of Malignant Glioma Cells With 2-5A-Antisense Telomerase RNA and Recombinant Adenovirus p53, Gene Therapy, (Dec. 2000), pp. 2071-2079, 7(24).

Kondraganti et al., Selective Suppression of Matrix Metalloproteinase-9 in Human Glioblastoma Cells by Antisense Gene Transfer Impairs Glioblastoma Cell Invasion, Cancer Research, (Dec. 15, 2000), pp. 6851-6855, 60(24).

Kulla et al., Tenascin Expression Patterns and Cells of Monocyte Lineage: Relationship in Human Gliomas, Modern Pathology, (Jan. 2000), pp. 56-87, 13(1).

Lacerra et al., Restoration of Hemoglobin A Synthesis in Erythroid Cells From Peripheral Blood of Thalassemic Patients, Proceedings of the National Academy of Sciences USA, (Aug. 15, 2000), pp. 9591-9596, 97(17).

Lal et al., A Public Database for Gene Expression in Human Cancers. Cancer Research, (Nov. 1, 1999), pp. 5403-5407, 59(21).

Ljubimov et al., Human Corneal Basement Membrane Heterogeneity: Topographical Differences in the Expression of Type IV Collagen and Laminin Isoforms, Lab Investigation, (Apr. 1995), pp. 461-473, 72(4).

Ljubimova et al., Gene Array Analysis of Differentially Expressed Genes in Human Glial Tumors. International Journal of Oncology, (2001), pp. 287-295, 18.

Ljubimova et al., Overexpression of a4 Chain-Containing Laminins in Human Glial Tumors Identified by Gene Microarray Analysis, Cancer Research (Jul. 15, 2001), pp. 5601-5610, 61(14).

MacDonald et al., Urokinase Induces Receptor Mediated Brain Tumor Cell Migration and Invasion, Journal of Neuro-Oncology, (Dec. 1998), pp. 215-226, 40(3).

McKean et al., FAK Induces Expression of Prx1 to Promote Tenascin-C-Dependent Fibroblast Migration, Journal of Cell Biology, (Apr. 28, 2003), pp. 393-402, 161(2).

Minakawa et al., In Vitro Interaction of Astrocytes and Pericytes With Capillary-Like Structures of Brain Microvessel Endothelium, Lab Investigation, (Jul. 1991), pp. 32-40, 65(1).

Miner et al., The Laminin Alpha Chains: Expression, Developmental Transitions, and Chromosomal Locations of A1-5, Identification of Heterotrimeric Laminins 8-11, and Cloning of a Novel a3 Isoform, Journal of Cell Biology, (May 5, 1997), pp. 685-701, 137(3).

Nielsen et al., Peptide Nucleic Acid Targeting of Double-Stranded DNA. Methods in Enzymology, 2001, pp. 329-340, 340.

Patarroyo et al., Laminin Isoforms in Tumor Invasion, Angiogenesis and Metastasis, Seminars . Seminars in Cancer Biology, (Jun. 2002), pp. 197-207, 12(3).

Petajaniemi et al., Localization of Laminin a4-Chain in Developing and Adult Human Tissues, The Journal of Histochemistry and Cytochemistry, (Aug. 2002), pp. 1113-1130, 50(8).

Qin et al., The Transcription Factors Sp1, Sp3, and AP-2 are Required for Constitutive Matrix Metalloproteinase-2 Gene Expression in Astroglioma Cells, Journal of Biological Chemistry, (Oct. 8, 1999), pp. 29130-29137, 274(41).

Sehgal, A., Molecular Changes During the Genesis of Human Gliomas, Seminars in Surgical Oncology, (Jan.-Feb. 1998), pp. 3-12, 14(1).

Shi et al., Antisense Imaging of Gene Expression in the Brain In Vivo, Proceeding of National Academy of Sciences USA, (Dec. 19, 2000), pp. 14709-14714, 97(26).

Sixt et al., Endothelial Cell Laminin Isoforms, Laminins 8 and 10, Play Decisive Roles in T Cell Recruitment Across the Blood-Brain Barrier in Experimental Autoimmune Encephalomyelitis, Journal of Cell Biology, (May 28, 2001), pp. 933-946, 153(5).

Summerton et al., Morpholino Antisense Oligomers: Design, Preparation and Properties, Antisense and Nucleic Acid Drug Development, (Jun. 1997) pp. 187-195, 7(3).

Taylor et al., Comparison of Efficacy of Antisense Oligomers Directed Toward TNF-a in Helper T and Macrophage Cell Lines, Cytokine, (Sep. 1997), pp. 672-681, 9(9).

Thyboll et al., Deletion of the Laminin a4 Chain Leads to Impaired Microvessel Maturation, Molecular and Cellular Biology, (Feb. 2002), pp. 1194-1202, 22(4).

Tsuji et al., Regulation of Melanoma Cell Migration and Invasion by Laminin-5 and a3β1 lntegrin (VLA-3), Clinical and Experimental Metastasis, (2002), pp. 127-134, 19(2).

Voyta et al., Identification and Isolation of Endothelial Cells Based on Their Increased Uptake of Acetylated-Low Density Lipoprotein, Journal of Cell Biology, (Dec. 1984), pp. 2034-2040, 99(6).

Zagzag et al., Angiogenesis in the Central Nervous System: A Role for Vascular Endothelial Growth Factor/Vascular Permeability Factor and Tenascin-C. Common Molecular Effectors in Cerebral Neoplastic and Non-Neoplastic "Angiogenic Diseases", Histol Histopathol, 17: 301-321, 2002.

Agrawal et al., Antisense Therapeutics: Is It As Simple As Complementary Base Recognition?, Molecular Medicine Today, (Feb. 2000), pp. 72-81, 6.

Gewirtz et al., Facilitating Oligonucleotide Delivery: Helping Antisense Deliver on Its Promise, Proceedings of the National Academy of Sciences of USA, (Apr. 1996), pp. 3161-3163, 93.

Fujita et al., Inhibition of Laminin-8 In Vivo Using a Novel Poly(Malic Acid)-Based Carrier Reduces Glioma Angiogenesis, Angiogenisis, (2006), pp. 183-191, 9.

Khazenzon et al., Antisense Inhibition of Laminin-8 Expression Reduces Invasion of Human Gliomas In Vitro, Molecular Cancer Therapeutics, (2003), pp. 985-994, 2.

Lu et al., Delivering siRNA In Vivo for Functional Genomics and Novel Therapeutics, RNA Interference Technology, (2005), pp. 303-317.

Nielsen, P.E., The Last Hurdle?, Gene Therapy, (2005), pp. 956-957, 12.

Samarsky et al., RNAi in Drug Development: Practical Considerations, RNA Interference Technology, (2005), pp. 384-395.

Bickel et al., Delivery of Peptides and Proteins Through the Blood-Brain Barrier, Advanced Drug Delivery Reviews, (2001), pp. 247-279, 46.

Boado et al., Drug Delivery of Antisense Molecules to the Brain for Treatment of Alzheimer's Disease and Cerebral AIDS, Journal of Pharmalogical Science, (1998), pp. 1308-1315, 87.

Broadwell et al., Transcytosis of Protein Through the Mammalian Cerebral Epithelium and Endothelium III Receptor-Mediated Transcytosis Through the Blood-Brain-Barrier of Blood-Borne Transferrin and Antibody Against the Transferrin Receptor, Experimental Neurology, (1996), pp. 47-85, 142.

Bulmus et al., A New pH-Responsive and Gluthathione-Reactive, Endosomal Membrane-Siruptive Polymeric Carrier for Intracellular Delivery of Biomolecular Drugs, Journal of Controlled Release, (2003), pp. 105-120, 93.

Cammas et al., Polymers of Malic Acid and 3-Alkylmalic Acid As Synthetic PHAs in the Design of Biocompatible Hydrolyzable Devices, International Journal of Biological Macromolecules, (1999), pp. 273-282, 25.

Fischer et al., An Unsual Polyanion From Physarum Polycephalum That Inhibits Homologous DNA Polymerase A In Vitro, Biochemistry, (1989), pp. 5219-5226, 28.

Iwata et al., A Novel Surgical Glue Composed of Gelatin and N-Hydroxysuccinimide Activate Poly(L-Glutamic Acid): Part 1 Synthesis of Activated Poly(L-Glutamic Acid) and Its Gelation With Gelatin, Biomaterials, (1998), pp. 1869-1876, .19.

Kopecek et al., HPMA Copolymer-Anticancer Drug Conjugates: Design, Activity, and Mechanism of Action, European Journal of Biopharmacology, (2000). pp. 61-81, 50.

Korherr et al., Poly ($\beta$-1-Malate) Hydrolase From Plasmodia of Physarum Polycephalum, Canadian Journal of Microbiology, (1995), pp. 192-199, 41(Suppl. 1).

Kurihara et al., Epidermal Growth Factor Radiopharmaceuticals: 111m Cheladon, Conjugation to a Blood-Brain Barrier Delivery Vector Via A Biotin-Polyethylene Linker, Pharmacokinetics, and In Vivo Imaging of Experimental Brain Tumors, Bioconjugate Chemistry, (1999), pp. 505-511, 10.

Lee et al., Effects of Culture Conditions on $\beta$-Poly (I-Malate) Production by Physarum Polycephalum, Applied Microbiology and Biotechnology, (1999). pp. 647-652, 51.

Pichon et al., Histidine-Rich Peptides and Polymers for Nucleic Acid Delivery, Advanced Drug Delivery Reviews, (2001), pp. 75-94, 53.

Saito et al., Drug Delivery Strategy Utilizing Conjugation Via Reversible Disulfide Linkages: Role and Site of Cellular Reducing Activities, Advanced Drug Delivery Reviews, (2003), pp. 199-215, 55.

Schnaible et al., Identification of Fluorescein-5'-Isothiocyanate-Modification Sites in Proteins by Electrospray-Ionization Mass Spectroscopy, Bioconjugate Chemistry, (1999), pp. 881-866, 10.

Shi et al., Noninvasive Gene Targeting to the Brain, Proceedings of the National Academy of Sciences, (2000), pp. 7567-7572, 97.

Willner et al., (6-Maleimidocaproyl) Hydrazone of Doxorubicin—A New Derivative for the Preparation of Immunoconjugates of Doxotubicin, Bioconjugate Chemistry, (1993), pp. 521-527, 1993.

Abdellaoui et al., Metabolite-derived Artificial Polymers Designed for Drug Targeting, Cell Penetration and Bioresorption, European Journal of Pharmaceutical Sciences, vol. 6, No. 1 (1998), pp. 61-73.

Barbosa, et al., Investigation of the Degradation Mechanisms of Poly(malic acid) Esters in Vitro and their Related Cytotoxicities on J774 Macrophages, Biomacromolecules 2004, vol. 5, No. 1, pp. 137-143.

Qian et al., Targeted Drug Delivery via the Transferrin Receptor-mediated Endocytosis Pathway, Pharmacology Reviews, vol. 54, No. 4, (Dec. 2002), pp. 561-587.

Zhang et al., Antisense Gene Therapy of Brain Cancer with an Artificial Virus Gene Delivery System, Molecular Therapy, vol. 6, No. 1 (Jul. 2002), pp. 67-72.

Ljubimova, J. et al., Changes in Laminin Isoforms Associated with Brain Tumor Invasion and Angiogenesis, Frontiers in Bioscience (Jan. 1, 2006), vol. 11, pp. 81-88.

Ljubimova, J., Black, K., Holler, E., Development of Anti-Angiogenic and Anti-Invasive Inhibitors of Human Gliomas Using a New Multifunctional Drug Delivery System Based on Polymalic Acid, Preclinica (Sep./Oct. 2004), 2(5), p. 366.

Ljubimova, J. et al., Association between Laminin-8 and Glial Tumor Grade, Recurrence, and Patient Survival, Cancer (online Jun. 16, 2004), 101(3), pp. 604-612.

Nagato, et al., Downregulations of Laminin $\alpha$-4 Chain Expression Inhibits Glioma Invasion in vitro and in vivo, Int. Journal of Cancer (Oct. 20, 2005), 117(1), pp. 41-50.

Fukushima et al., Integrin $\alpha 3\beta 1$-mediated Interaction with Laminin-5 Stimulates Adhesion, Migration and Invasion of Malignant Glioma Cells, Int. of Journal Cancer (Mar. 30, 1998), 76(1), pp. 63-72.

Lee et al., Delivery of antisense oligonucleotides and transferrin receptor antibody in vitro and in vivo using a new multifunctional drug delivery system based on polymalic acid, Proceedings of The American Association for Cancer Research Annual Meeting, vol. 45, Mar. 2004, XP8120390, pp. 149-150.

* cited by examiner

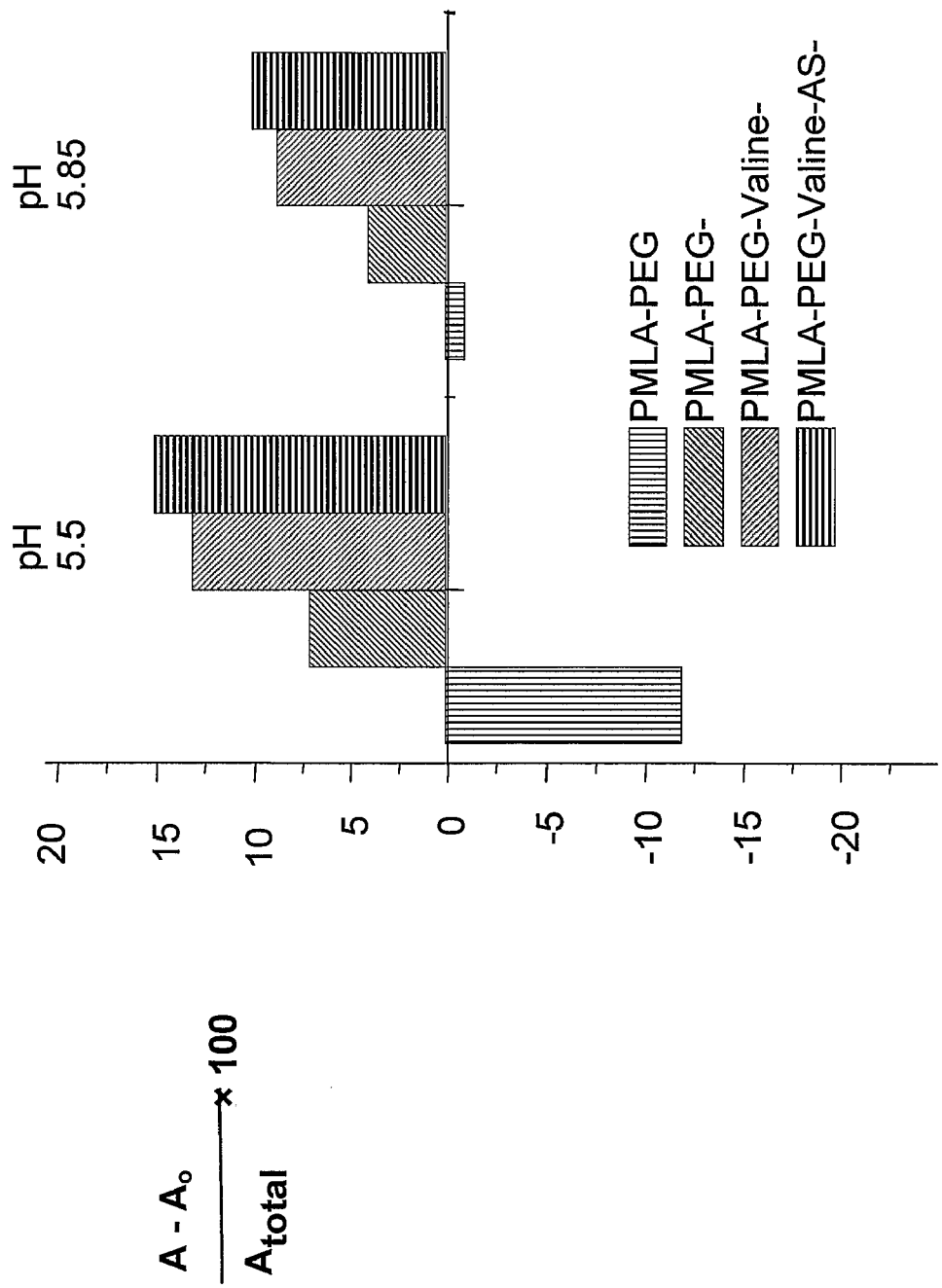

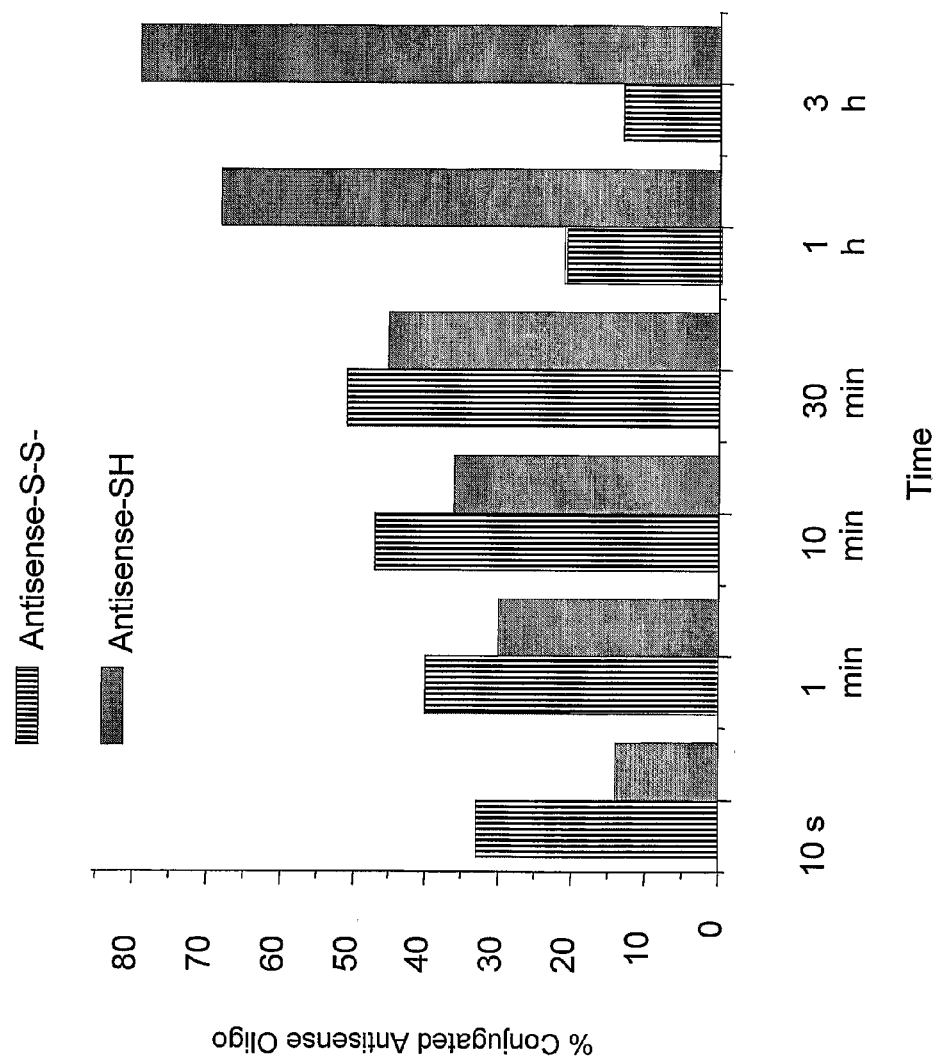

Fig. 17
Normal rat brain
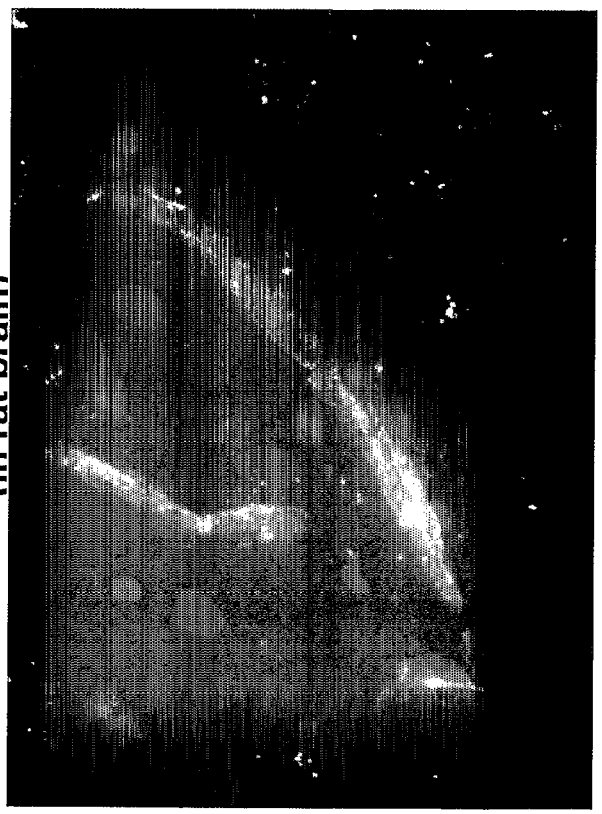
U87MG tumor
(in rat brain)

POLYMALIC ACID-BASED MULTI-FUNCTIONAL DRUG DELIVERY SYSTEM

This application is the National Phase of International Application PCT/US04/40660, filed Dec. 3, 2004, which designated the U.S. and that International Application was published under PCT Article 21(2) in English. This application also includes a claim of priority under 35 U.S.C. §119(e) to U.S. provisional patent application No. 60/527,330, filed Dec. 5, 2003.

The present application is based on U.S. Provisional Patent Application Ser. No. 60/527,330 filed 5 Dec. 2003 and claims priority from that application.

BACKGROUND OF THE INVENTION AND DESCRIPTION OF THE PRIOR ART

The present invention relates to the field of targeted delivery of drugs and more specifically involves a multifunctional targeted drug delivery vehicle.

Currently several different molecular scaffolds are used in the synthesis of drug vehicles; notable examples are N-(2-hydroxypropyl)methacrylamide (HPMA) copolymer (20-30 kDa) [42] and other derivatives of polyacrylic acid. However, these are not considered to be biodegradable [43, and references therein], because of their carbon-carbon backbone, and they are problematic due to inevitable contamination by hazardous acrylic acid [44]. Other, degradable scaffolds (e.g. poly(L-glutamic acid) [45] may have unfavorable properties, like rotational restriction around the peptide bond or limited solubility in organic solvents desirable for chemical synthesis and product purification, and, in addition, is supportive of immunogenicity in the structural proximity to other potentially immunogenic structures due to the high hydrogen bond forming capacity of the peptide backbone [45, 46, 47].

Antisense Technology. Antisense oligonucleotides (oligos) that bind and inactivate specific RNA sequences may be one of the best tools for studying gene function, regulation of gene expression, interactions between gene products, and validation of new therapeutic targets for drug development. Antisense oligos offer the promise of safe and effective therapeutics for viral diseases, cancers, and other devastating diseases. Specific antisense oligos that mimic DNA template for RNA production are used to bind to complementary RNA and to prevent protein translation (e.g., of tumor markers) [1].

There are promising data on the use of antisense technology in gliomas. Glioma growth in vitro and in nude mice can be inhibited by antisense to telomerase [2]. A pilot study showed that antisense to IGF-I receptor induced glioma cell apoptosis and resulted in clinical improvements of patients [3]. Several clinical trials are currently using antisense oligos for treatment of other cancers [4]. These studies take advantage of new generation antisense oligos free from insufficient specificity, stability, and non-antisense effects [5]. The most promising varieties of improved oligos are Morpholinos oligos and peptide nucleic acid (PNA) oligos. These varieties have the highest sequence specificity of all antisense types, and maintain this specificity over a very broad concentration range [6, 7, 8, 9, 10 and 11]. A new, rapidly evolving, variant of antisense approach is represented by small interfering RNAs (siRNAs) that are also highly potent gene expression silencers and potential anticancer drugs.

Combined blocking of several molecular markers in vitro and in vivo to prevent tumor progression. This approach has long been used successfully in cancer chemotherapy but has not yet been applied to targeting specific tumor markers. Only following the development of gene/protein array approaches, did it became possible to obtain and correlate data on concerted changes of specific genes during tumor progression and recurrence. Such concerted changes offer a possibility of counteracting simultaneous alterations of several genes in the hope of efficiently blocking tumor development and progression. There are several candidate genes for blocking to stop glioma growth and spread including tyrosine kinase receptors (e.g., EGFR), some growth factors, and antiapoptotic genes that can be potentially used in combination with chemotherapeutic agents to more efficiently prevent tumor growth [12, 13, 14, 15, and 16]. Our earlier studies identified another potential candidate protein, laminin-8, which is overexpressed in brain and breast tumors, correlates with poor prognosis of gliomas and is involved in glioma invasion.

Drug delivery. For direct targeting of cancer cells to treat tumors, the drugs, e.g., monoclonal antibodies, antisense oligos or small molecules (such as Tarceva (erlotinib)), should be able to penetrate the cell membrane. There are three basic methods for intracellular drug delivery, passive diffusion through aqueous channels or pores in the membrane, passive diffusion of lipid-soluble drugs through dissolution in the lipids of the membrane, and carrier-mediated active transport (viral vectors, liposome-mediated gene transfer system, special chemicals) [16, 17]. Brain tissue is especially difficult to treat with drugs because it has a special blood brain barrier with tight junctions between brain microvascular endothelial cells that prevent penetration of water-soluble and ionized or polar drugs [18, 19].

High molecular weight molecules have recently received special attention because of the enhanced permeability and retention (EPR) effect observed in cancer tissue for macromolecules and lipids (MW>45 kDa) [20, 21, and 22]. Unlike small molecule anticancer drugs used today, which do not discriminate tumor from normal tissue, macromolecular (or polymeric) drugs can target tumors with high selectivity through the EPR effect [22, 23]. One such promising drug carriers, poly-L-malic acid (PMLA), has been developed by one of the present inventors [24, 25].

SUMMARY OF THE INVENTION

It is an object of the invention is to solve the problems that have formerly plagued drug carrier systems by using polymalic acid, which carries an abundance of functional carboxylic groups, at least about 50 of such groups and about 500 per polymalic acid molecule of mass 50,000. The polymalic acid is readily available in a range of sizes from a molecular mass of 2,500 to at least 100,000. This allows the attachment of a large number of biologically active functional molecular modules to achieve:

a high variability in the kind and number of tissue targeting molecules per drug carrier molecule;
  a high variability in the kind and number of conjugated drug modules (pro-drugs) per drug carrier molecule;
  an ability to control solubility by having groups carrying either hydrophobic or hydrophilic residues in addition to the functional modules;
  an ability to conjugate, other than the described functional modules, additional groups, such as PEG, which are active in protection of the carrier system against degradation e.g., to increase lifetime in the blood circulation system;
  a carrier scaffold that is biodegradable, along with many other residues used as building units of the drug delivery system;
  a system with no use of viral components;

a delivery system with functional modules (mABs or other tumor cell surface receptor ligands), the kind of drug (antisense oligonucleotides to malignantly expressed genes), and a totally high molecular mass of the drug delivery system account for high specificity towards tumor tissue (EPR-effect); and a drug system of low toxicity allowing rat dosages as high as 5 mg/kg rat body weight.

A further object of the invention is:

to facilitate synthesis of a drug delivery system by avoiding convoluted synthetic methods and uncontrollable side reactions;

to build in favorable solubility and other properties that provide an easy purification;

to achieve maximum yields that allow defined stoichiometry and the reproducibility of each individual chemical conjugation reaction;

to lay the structural and synthetic fundaments for a high variability regarding the kind and number of conjugated functional modules; and to provide a technology that allows simple scale up of the drug delivery system.

The technical invention includes:

the choice of drug delivery system employing polymalic acid as a backbone or scaffold that carries a very high number of reactive carboxylic groups (about 500 for a scaffold of molecular mass 50,000);

activation of most (ideally all) of these carboxylic groups by forming their NHS-esters;

chemically independent preparation of functional modules, which carry single amino groups as nucleophiles for substitution at the NHS-activated carboxyl groups;

preparing the activated scaffold and each of the reactive functional modules separately;

combining and reacting the NHS-activated scaffold and each reactive functional module independent but in a well defined sequential order, allowing purification and verification of the desired intermediates/products after each addition of a newly added functional module;

combining these reactants in stoichiometric amounts;

achieving high and reproducible yields of conjugates; and avoiding side reactions of newly added reactive functional modules with the already conjugated modules by choosing a well organized hierarchy of sequential additions for the conjugation of the next incoming functional modules.

The design and synthesis of a carrier or scaffold is described, which transports a covalently conjugated drug to a targeted tissue, binds to cell surface receptors of the tissue, internalizes into endosomes, escapes the endosomes into the cytoplasm, and releases reactive free drug in the cytoplasm by chemical reaction with glutathion and other sulfhydryl groups of the cytoplasmic content. The specificity of high molecular mass drug vehicles or even particles rests on the both the tumor tissue targeting by tumor-specific conjugated targeting molecules and their enhanced permeability and retention in tumors (EPR-effect) that solely originates from their high molecular mass (>20000) [40, 41].

The scaffold poly(malic acid) (PMLAH) used in the present patent application contains a main chain ester linkage, is biodegradable [27, and references therein] and of a high molecular flexibility [49], soluble in water (when ionized) and organic solvents (in its acid form), non-toxic, and non-immunogenic [27, and references therein]). Drug carrying PMLAH has been mainly synthesized by ring-opening polymerization of derivatized malic acid lactones [27, and references therein]. Synthesis of Doxorubicin-poly(malic acid) has been reported from chemically synthesized poly(β-D, L-malic acid) [49]. The synthesis of drug vehicle from naturally occurring PMLAH has not been carried out. The kind of highly functional drug delivery system described in the present patent application has not been previously disclosed.

The carrier consists of poly(β-L-malic acid) (PMLA) representing the molecular backbone or scaffold that is chemically conjugated at its carboxylic groups at defined ratios with a variety of functional modules that perform the following tasks: (1) delivery of a pro-drug via a releasable functional module that becomes effective in the cytoplasm, (2) directing the carrier towards a specific tissue by binding to the surfaces of cells (e.g. a monoclonal antibody (mAB)), (3) internalization into the targeted cell through endosomes (usually via internalization of a targeted surface receptor), (4) escape from endosomes into the cytoplasm by virtue of hydrophobic functional units that integrate into and finally disrupt endosomal membranes, becoming effective during acidification of endosomes en route to lysosomes, (5) protection by polyethylene glycol (PEG) against degradative enzyme activities (e.g. peptidases, proteases, etc.).

In this invention a "module" is a biologically active molecular structure ranging from a small drug molecule or chromophore molecule to a complete protein molecule such as an antibody or lectin. In the case of the examples presented herein (1) is represented by morpholino antisense oligonucleotides against α-4 chain and β-1 chain of laminin-8 [34, 51] coupled to an intervening spacer by an amide linkage by means of an —$NH_2$ (amino) group artificially introduced at their 3'-termini. The spacer is attached to the carrier by a disulfide moiety that is cleavable in the sulfhydryl-disulfide exchange reaction with glutathion in the reducing milieu of the cytoplasm [51, 52]. (2) Tissue targeting is designed by employing a monoclonal antibody (mAB) to recognize and bind rat transferrin receptor. This receptor has been found expressed on endothelium cell surfaces that function as the blood brain barrier (BBB), and at elevated levels on certain tumors [53, 54]. In vitro and in vivo studies indicate that transferrin receptor may be used as an anchorage for a drug delivery system chemically bound to transferrin or mAB OX-26 or any other appropriate mAB that binds the transferrin receptor and thereby achieves transcytosis through blood brain barrier (BBB) of rat or mouse or other mammals depending of the allotype of the antibody [5, 56, 57; 45, 58, 59, 60, and 61]. (3) Antibody binding to transferrin receptor and internalization into endosomes has been demonstrated [57, 55, and 57. It will be appreciated that in the case of the transferrin receptor any appropriate antibody, mAB, humanized or chimeric antibody or lectin or other ligand specific to the transferrin receptor can be used. It is also appreciated that appropriate ligands to any number of cell surface receptors or antigens can be used in the invention and that transferrin receptor is merely an example. (4) Endosomal escape has been shown to function for polyacrylic acid derivatives by acidification during maturation of the endosomal vesicles towards lysosomes [51, 62]. The designed carrier proposed in this patent application carries an abundance of valine residues linked to the polymalic acid scaffold by amide bonds. During acidification of the endosomes en route to lysosomes, these stretches of the carrier molecule become charge-neutralized and hydrophobic, and are capable to disrupt membranes. Other molecules may be used in place of valine so long as they become charge neutralized at lysomal pH's. (5) PEGylation markedly increases the half-life of conjugated proteins [63], prolongs the circulation time, and enhances extravasation into targeted solid tumors [64]. Any other molecule know to increase half-life may be used in the invention.

DESCRIPTION OF THE FIGURES

FIG. 1b shows the overall sequence of steps used to assemble the structure of FIG. 1a.

FIG. 9 shows a bar graph of the results of a hemolytic assay used in testing the polymers.

FIG. 10a shows the release of morpholino oligos from the carrier by means of reduction with glutathione.

FIG. 17 shows that Drug 2 is capable of crossing the BBB where the red color represents the drug visualized within brain vessels and transplanted tumor cells following intravascular administration of the drug.

DETAILED DESCRIPTION OF THE INVENTION

Figure 1A:
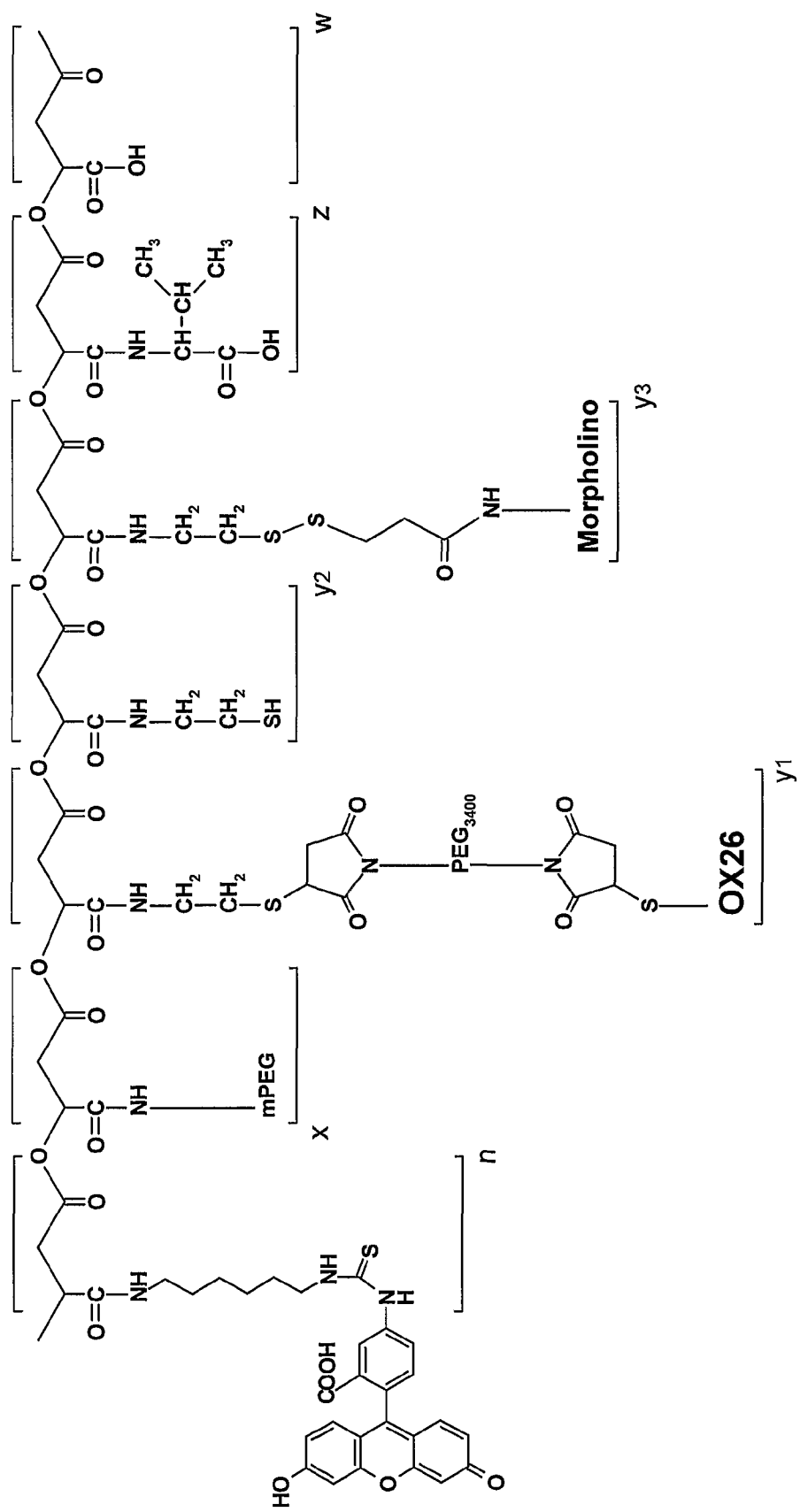
FIG. 1a shows the overall structure of a drug molecule of the present invention.

The following description is provided to enable any person skilled in the art to make and use the invention and sets forth the best modes contemplated by the inventor of carrying out his invention. Various modifications, however, will remain readily apparent to those skilled in the art since the general principles of the present invention have been defined herein specifically to provide a novel drug delivery system as exemplified by an antisense anti-tumor drug based on poly-L-malic acid.

The attractive properties of PMLA as a carrier matrix or molecular transport vehicle for pharmaceuticals and biopharmaceuticals are the following: it is non-toxic and non-immunogenic; its hydrophobicity can be controlled by introducing hydrophobic side chains or spacers [30]; it is biodegradable [31]; and it is stable in bloodstream. For targeting antisense oligos to a specific organ or compartment, targeting entities such as tumor-specific antibodies that favor receptor-mediated endocytosis can be conjugated to the PMLA polymer. Ideally, the system includes a releasing system for releasing the drug from the molecular transport vehicle; possible releasing systems include: a) a disulfide bond cleavable by the intracellular glutathione, b) a pH-sensitive hydrazone bond, c) a tetrapeptide cleaved by lysosomal cathepsin B, which activity is elevated in various tumors (or other pepidases); d) an intrinsic release function from endosome [32, 33]; and e) other labile or cleavable bonds such as ester linkages. Most importantly, inhibitors of multiple molecular targets can be easily attached to one PMLA molecule.

PMLA from the natural source, plasmodia of *Physarum polycephalum* [27 and references therein], was the starting material for the synthesis of the drug delivery vehicle described in the present patent application. The methods of chemical syntheses employed here are from the general fundus of methods in synthetic chemistry, and have been described in other systems, not related to the polymalic acid-based system described here. Most of these methods had to be adapted to the present situation, in particular to the properties of educts during the progress of the chemical construction of the carrier system, and with regard to the methods of purification of products. To achieve a successful derivatization with a predictable and reproducible stoichiometry of the functional moieties conjugated to the polymalic acid scaffold, the sequence of the reactions with the scaffold had to be established and organized in such a way, that an uncontrolled reaction was impossible. The validity of products has been achieved and the purity controlled by in situ analysis during the stepwise synthesis, including qualitative and quantitative chemical assays, high performance liquid chromatography (HPLC), thin layer chromatography (TLC), and ultraviolet/visible/IR light spectroscopic analyses as well as NMR-spectroscopic methods. The membrane disruption properties of the fully assembled drug vehicle and also of the intermediates of its synthesis was assessed by a routine, empirical hemolytic membrane assay [see 51].

The references of standard synthesis methods underlying the development of the methods used here are in particular:

Activation of PMLAH-carboxylic groups as N-hydroxysuccinimide (NHS) esters in analogy to the method of [69].

Coupling of the (2-pyridyldithio)propionyl group to morpholino (PDP)-morpholino) antisense oligonucleotides in analogy to the method described in [51 and references therein].

FITC (fluorescein isothiocyanate)-conjugation in analogy to the method for the formation of N-(fluorescein-5'-thiocarbamyl)diaminohexane of [71].

Synthesis of N,N'-bis-(3-maleimidopropionyl)poly(ethylene glycol) in analogy to the method of [70].

Introduction of thiol groups into antibodies in analogy to the techniques described of [72, 51 and references therein].

Reaction of mAB OX-26-sulfhydryl with N,N'-bis-(3-maleimidopropionyl)-PEG diamide conjugate were performed in analogy to the reactions carried out in [52, and 69].

Synthesis of PMLA/L-valine/2-mercaptoethylamine/mPEG-NH2 conjugate by amide formation from the NHS-activated carboxylate was carried out principally as described herein.

Synthesis of PMLA/mAB OX-26/morpholino antisense oligonucleotide/L-valine/2-mercaptoethylamine/mPEG-NH2 conjugate by reaction of sulfhydryl group with maleimide;

Conjugation of FITC-spacer to PMLA/mAB OX-26/morpholino antisense oligonucleotide/L-valine/2-mercaptoethylamine/mPEG-NH2 conjugate, represented in principal an amide formation by nucleophilic attack of the NHS-activated carboxylate as described herein.

Existing drug delivery systems suffer from one or several of the following problems:
  They are not multifunctional, i.e. they are limited with regard to variability in the kind and amount of tissue targeting groups per carrier molecule;
  They are limited by the kind and number of conjugated drugs (pro-drugs) per carrier molecule;
  They are limited by solubility in physiological fluids;
  They are limited by insufficient stability against degradation in the circulation system;
  They are not biodegradable;
  They involve viral nucleic acids or other viral fragments;
  They are not specific for tumor tissue and they damage healthy host tissue
  They are toxic;
  The synthesis of the drug delivery system suffers from uncontrollable side reactions;
  The synthesis of the drug delivery system suffers from solubility or other problems that render purification of reaction products difficult or impossible;
  The synthesis of the drug delivery system does not result in reproducible products;
  The synthesis of structural variations/extension to contain new components, thus enhancing specificity or sharpening the antitumor activity of the drug delivery system is not possible; and
  The synthesis of the drug delivery system cannot be readily scaled up.

The controlled conjugation of each reactive functional module with the NHS(N-hydroxysuccinimide) activated carboxylic groups of the polymalic acid scaffold allows one to conjugate a variation of different kinds of reactive functional modules, thus introducing a variety of different targeting molecules, drug (pro-drug) molecules, etc. The various modules can be conjugated to one and the same scaffold molecule or to different ones allowing a binary or ternary, etc. drug mixture. Multiple functional modules on one and the same scaffold molecule can display biologically synergistic effects when simultaneously being introduced into the cell.

Biodegradability can be achieved by employing biodegradable polymalic acid as scaffold and other biodegradable building units (amino acids, proteins).

DESCRIPTION OF THE INVENTION BY A SPECIFIC EXAMPLE

Figure 1B:
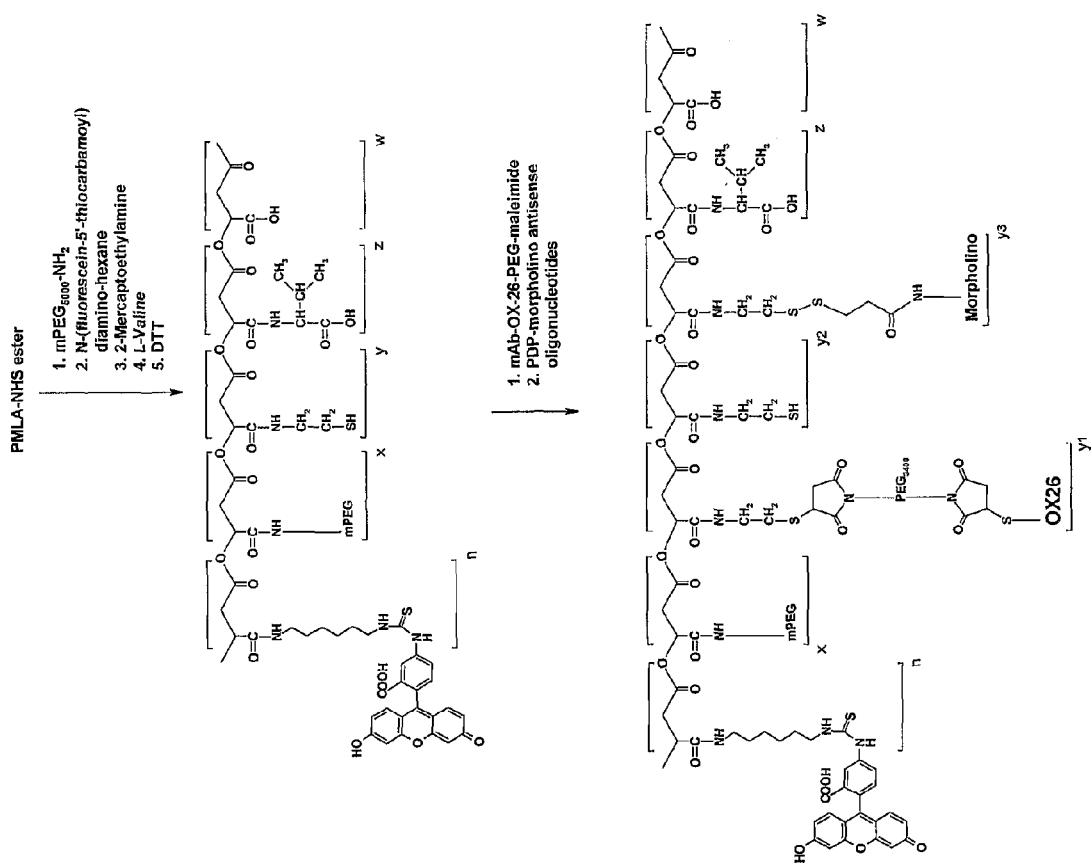

Synthesis of a Polymalic Acid Based Multifunctional Carrier System for the Tumor Targeted Delivery of Morpholino Antisense Oligonucleotides FIG. 1a shows the overall structure of a typical drug molecule of the present invention. For the synthesis of Block (z+w), the carboxyl groups of polymalic acid (block w) are activated as NHS-esters and conjugated to L-valine via amide bond. Block y3 is the pro-drug morpholino antisense oligos containing a disulfide drug releasing unit. Block y1 is the monoclonal antibody (OX26) targeting molecule conjugated to the block z+w via polyethylene glycol (PEG) spacer. Block x is the PEG-protector against degradation, attached by an amide bond and formed from commercially available PEG-amine. Block y2 represents remaining sulfhydryl anchor groups, which have not been consumed by the synthesis at this point, and which can be used for the conjugation of additional functional modules via reaction with the double bond of substituted N-ethylmaleimides or simply blocked by reaction with unsubstituted N-ethylamaleimide. Block n, the fluorescent reporter group, is prepared from fluorescein isothiocyanate (FITC) and N1-Boc-1,6-diaminohexane. The drug structure is built by a stepwise coupling of the blocks (i.e., the modules) onto the growing conjugate as shown in FIG. 1b under a careful stoichiometric control. The order of the steps can be readily adjusted to fit different scenarios. Conjugations are carried out with carbodiimide reagents in organic solvent, preferably dimethylformamide. Side reactions are prevented by appropriate protection of side chains following standard methods.

For Block w highly purified polymalic acid is obtained from cultures of *Physarum polycephalum* [24, 25]. The biopolymer is spontaneously and enzymatically degraded to L-malic acid [31, 26], which is metabolized to carbon dioxide and water. The sodium salt is neither toxic nor immunogenic in mice and rabbit respectively [27 and references therein]. After intravenous injection into mice, polymalate was rapidly cleared by excretion via the kidneys [73]. Certain polyymalate derivatives and block polymers actually showed positive effects on bone repair and muscle regeneration in rats [30] or were found biocompatible in other investigations [32]. Polymalic acid is an excellent candidate for the design of a drug carrier device, because of its high abundance of modifiable carboxyl groups. These can be easily conjugated to a variety of different biologically active molecules in a perfectly controllable fashion regarding their stoichiometry and integrity. Block z is based on polymers that contain lipophilic groups like L-valine or L-leucine and become increasingly lipohilic when protonated when ambient pH falls below pH 6 during maturation of endosomes to lysosomes. This increasing lipophilicity results in leakiness of the endosomal membranes and causes release of the macromolecular content into the cytoplasm [33, 74, 75]. Block y3 contains a disulfide bond, which is stable in blood circulation including brain microvessels but is cleaved in the reductive environment of the cells [38]. Block y1 contains a polyethylene glycol spacer that allows the tissue targeting moiety to bind to the receptor on the target cell surface. It also protects against degradation of the targeting polypeptide. (y3) The morpholino oligonucleotides, which specifically block the expression of tumor essential genes, such as the α1-chain of laminin are used. In principle, any other drug or pro-drug can be conjugated here, as well as an array of different drugs on a single carrier molecule. These conjugates are cleaved from the carrier at the drug releasing unit within the cytoplasm, and the drug(s) become effective. Block y1 helps breach the BBB which is targeted by a monoclonal antibody against the transferrin receptor on the endothelial cells of the BBB [55]. Bradykinin alone or conjugated together with other molecules, might also be a targeting molecule to be used for the brain tumors by virtue of specific receptors [77, 18, and 78]. A further possibility for the brain tumor specific targeting is to use a monoclonal antibody against the human EGF receptor [37, 79].

Bradykinin $B_2$ receptors and EGFR are overexpressed on tumor cells and can also be used as brain tumor targeting sites in combination with transferrin receptor. Block n adds an arbitrary fluorescent label, here fluorescein, which is conjugated to the drug structure to facilitate homing studies of the carrier in the endosomes of recipient tumor cells.

Materials and Methods

Poly($\beta$-L-malic acid) (PMLA) was purified from the broth of cultured *Physarum polycephalum* plasmodia using methods developed from [25]. The polymer in salt form was size fractionated on Sephadex G25 columns. The fraction with a number-averaged molecular mass of 50 kDa (polydispersity 1.2) was converted to the free polymer acid (PMLA-H) by passage over Amberlite IR-120 ($H^+$ form) and stored freeze-dried before used in carrier synthesis. $^1$H-NMR in $D_2O$ gave the following $\delta$-values: 3.3 ppm (doublet, the methylene protons of the polyester backbone), 5.3 ppm (triplet, the methine protons of the polyester backbone). Proton-broad-band-decoupled $^{13}$C-NMR gave the following $\delta$-values: 178.4 ppm (—COOH), 74.5 ppm (—CHOH—), 38.9 ppm (—CH$_2$—), and 174.5 ppm (—CO—). Purified PMLA-H shows UV-light absorbance only below 220 nm wavelength, and is devoid of absorbance at 260 and 280 typical for nucleic acids and proteins, respectively (further details are reviewed in [27]). Morpholino™-3'—NH$_2$ antisense oligonucleotides [6] to the $\alpha$-4 chain of laminin-8 (AGC-TCA-AAG-CCA-TTT-CTC-CGC-TGA-C) and to the $\beta$-1 chain of laminin-8 (CTA-GCA-ACT-GGA-GAA-GCC-CCA-TGC-C) [50, 34] were purchased from Gene Tools (USA). Mouse monoclonal antibody against rat transferrin receptor CD71 (clone OX-26, isotype IgG$_{2a}$) at a concentration of 1 mg/ml PBS containing 10 mM sodium azide was obtained from Chemicon Europe (UK). Mouse IgG$_{2a}$, $\kappa$(UPC 10) was purchased from Sigma (Germany). Chromatographically pure mPEG-amine (MW 5000) and amine-PEG-amine (MW 3400) were obtained from Nektar Therapeutics (USA). Reagents and solvents obtained from Merck (Germany), Sigma (Germany), Pierce (USA) were of the highest available purity. Dichloromethane (DCM) and N,N-dimethylformamide (DMF) were dried over molecular sieves (0.4 nm).

$^1$H-NMR spectra were recorded on a Bruker Model DMX-500 Fourier transform spectrometer and chemical shifts are given in ppm ($\delta$) relative to TMS as internal standard. $^{13}$C NMR spectra were recorded on the same spectrometer operated at 125.8 MHz. Chromatographic separations were performed with a Merck-Hitachi analytical LaChrom D-7000 HPLC-system equipped with UV and fluorescence detectors. Either Macherey & Nagel $C_{18}$-Nucleosil reversed-phase (RP) columns (250×4 mm) with a binary gradient of 0.1% TFA (trifluoroacetic acid) in water–0.07% TFA in acetonitrile at a flow rate of 1.5 ml/min or size exclusion columns Bio-Sil SEC 250-5 (5 µm, 300×7.8 mm) with 50 mM sodium phosphate buffer pH 7.4 at a flow rate of 0.75 ml/min were used. Molecular mass of the polymer Na or K-salt was determined by SEC-HPLC with polystyrene sulfonate standards of defined molecular weight (Machery-Nagel). Thin layer chromatography (TLC) was performed on Merck precoated silica gel 60 F254 aluminum sheets. The eluent contained a mixture of n-butanol, water, and acetic acid (4:2:1 on a volume ratio basis).

Syntheses

Synthesis of PMLA-NHS Ester 1.16 g of PMLA-H (10 mmol regarding the malic acid monomer) was dissolved in 30 ml of anhydrous dimethylformamide (DMF). N-hydroxysuccinimde (NHS) (15 mmol), dissolved in 10 m of anhydrous dimethylformamide (DMF), was added to the PMLA-H solution. The temperature was lowered to 0° C. in an ice bath, then dicyclohexylcarbodiimide (DCC) (15 mmol) dissolved in 10 ml of DMF was added. The reaction mixture was held under reduced pressure at room temperature until no gas bubbles developed. After 30 min at 0° C., the reaction mixture was stirred at room temperature for 48 h. The reaction mixture was held as described above under reduced pressure followed by incubation every 2 h during the first day of reaction, then every 6 h during the second day of reaction. After two days of reaction, dicyclohexylurea was removed by filtration, and the reaction volume was reduced by evaporation under reduced pressure. Fresh anhydrous DMF (10 ml) was added and residual dicyclohexylurea was again removed by filtration. The clear reaction mixture was stirred for 12 h at room temperature and last amounts of dicyclohexylurea (if any) were removed by filtration. The volume was reduced to 1-3 ml by evaporation under reduced pressure, and the product was precipitated by the addition of ethyl acetate. The pale yellow product (P1) was collected by filtration. Diethylether was added to the filtrate to match the final proportion of 1:1 (ethyl acetate:diethylether), and more of a light brown product was collected by filtration (P2). Then n-hexane was added to the filtrate to match the final proportion of 1:1:1 (ethyl acetate:diethylether:n-hexane) and additional brown product was collected by filtration (P3). The precipitates were dispersed in the same solvents used for their precipitation and left overnight in the cold (−20° C.). The products were filtered and washed repeatedly with the same cold solvents. The products were further purified by passage through Sephadex LH 20 using DMF as eluent allowing the flow by gravity. The product containing fractions were collected and the solvents evaporated under reduced pressure. Finally, the products were dispersed in diethylether, collected by filtration, dried in vacuo, and stored at −20° C.

Figure 2:
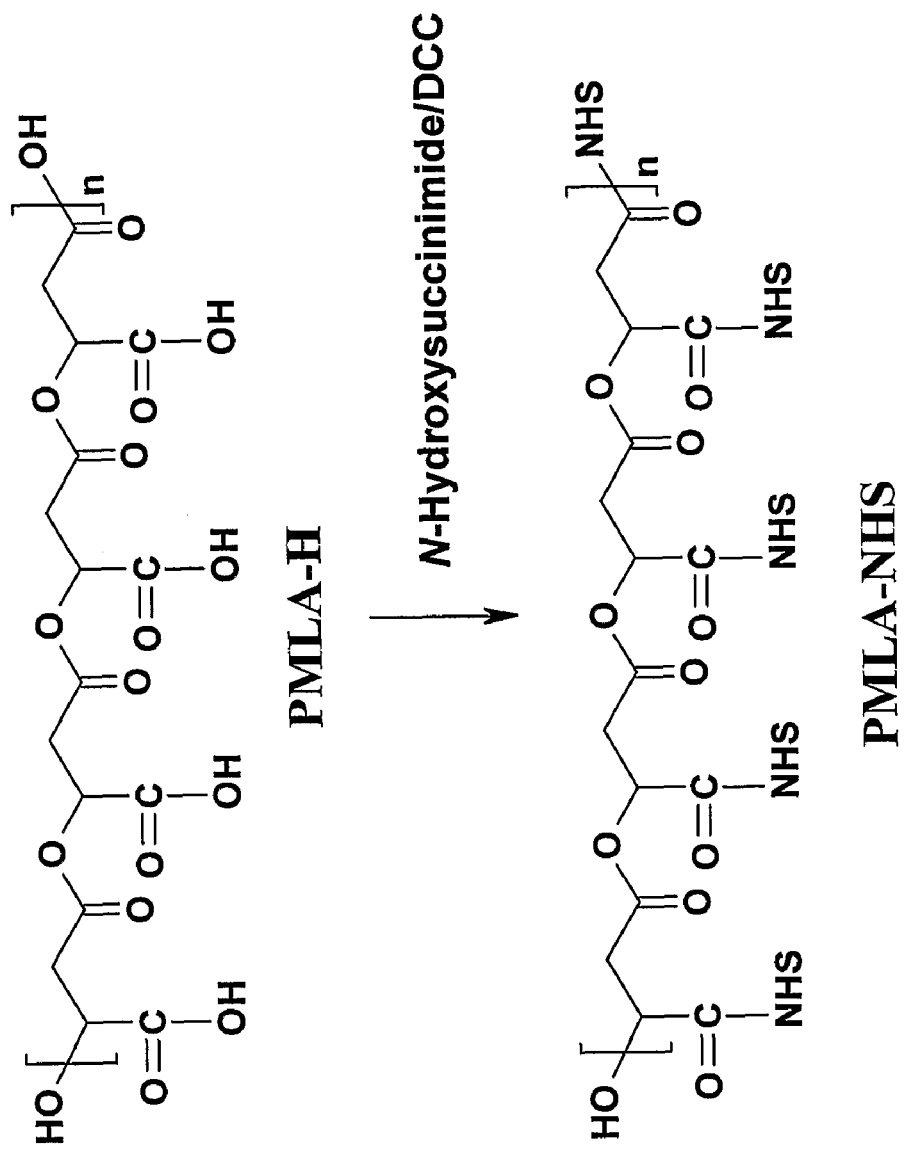
FIG. 2 is a diagram illustrating the synthesis of PMLA-NHS ester.

The purity/composition of these preparations of PMLA-NHS ester was analyzed by $^1$H NMR and UV-VIS spectroscopy. The content of NHS groups was determined after aminolysis of NHS ester groups with n-butylamine. 10 mg of PMLA-NHS ester were dissolved in 0.5 ml of DMF. A portion of 0.5 ml of 10% n-butylamine was added to this solution, and the reaction mixture was incubated at room temperature for 30 min. After centrifugation, samples of 20 µL were mixed with 80 µl of water and analyzed by RP-HPLC employing water/0.1% (v/v) TFA as eluent. NHS groups were monitored by their absorbance at 260 nm. Their content was calculated by comparing the absorbance with that of standards of known amounts of N-hydroxysuccinimide. The molar ratio of malic acid residues and NHS-groups in the PMLA-NHS ester sample was calculated by combining these results with the amounts of malyl residues measured by $^1$H-NMR. Typically, the ratios were 35, 59, and 85% for P1, P2, and P3, respectively. $^1$H NMR in $(CD_3)_2SO$ gave the following $\delta$-values: 2.8 ppm (singulet, 4H N—CO—CH2-), 3.35 ppm (doublet, the methylene protons of the polyester backbone), 5.85 ppm (triplet, the methine protons of the polyester backbone). The reaction is shown in FIG. 2.

Synthesis of (2-pyridyldithio)propionyl-morpholino (PDP-morpholino) Antisense Oligonucleotides Morpholino-3(—NH$_2$ antisense oligomer (1 µmol) was dissolved in a of 900 µL of DMF and 100 mL of deionized water. To this mixture, 20 µL of a 100 mM solution of N-succinimidyl 3×2-pyridyldithio)propionate (SPDP) in DMF was added and left for 2 h at room temperature. The solvent was removed by rotary evaporation under reduced pressure at room temperature. The residue was dissolved in 1 ml of buffer A (0.1 M sodium phosphate, 0.15 M NaCl, pH 7.2) containing 10 mM EDTA and purified over a Sephadex G-25 microspin column pre-equilibrated with buffer A. The concentration of PDP-morpholino antisense oligonucleotide was adjusted to 1 mM and stored at −20° C.

Figure 3:
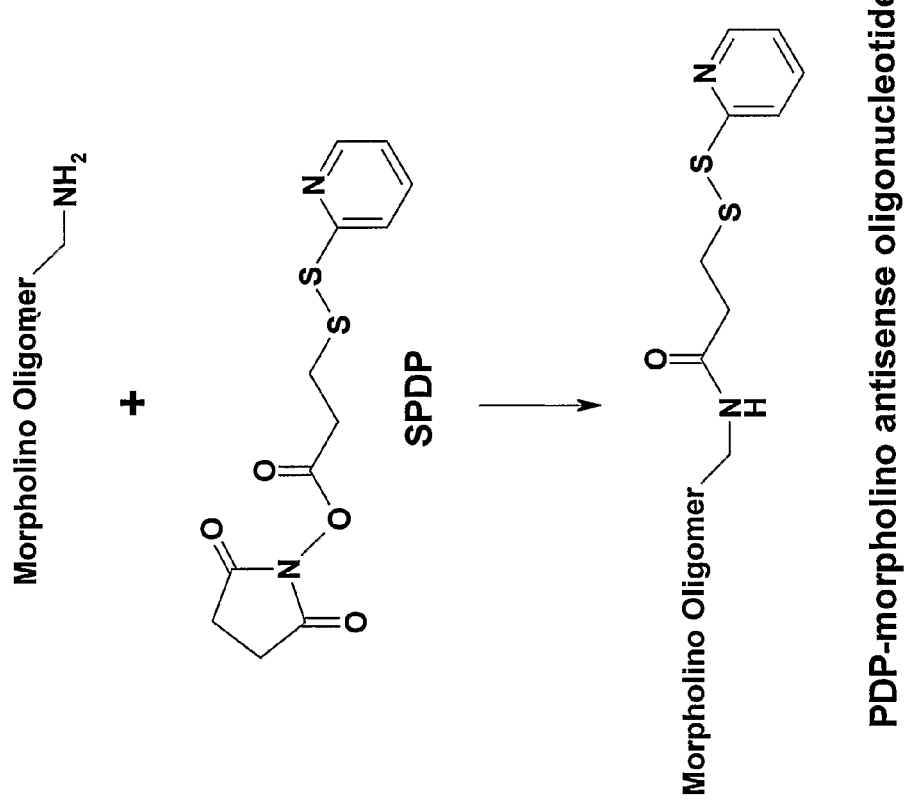
FIG. 3 is a diagram illustrating the synthesis of (PDP-morpholino) antisense oligonucleotides.

The purity of the product was confirmed by TLC and UV-spectroscopy by showing the absence of NHS and SPDP. The content of PDP groups was determined by measuring the concentration of 2-thiopyridone after disulfide reduction as follows: PDP-morpholino antisense oligonucleotide was incubated with 0.2 M dithiothreitol (DTT) in 0.1 M Tris buffer pH 9.0 for 30 min at room temperature. The reaction mixture was subjected to RP-HPLC by first washing for 10 min with distilled water and then eluting in 30 min with a gradient of 0-60% acetonitrile. The reaction product 2-thiopyridone was detected using UV absorption at 341 nm. The concentration of 2-thiopyridone was measured by using the absorbance of known amounts of reduced 2-aldrithiol (DPDS) as standards. The yield of PDP-morpholino antisense nucleotide was routinely higher than 80% of the starting amount of morpholino-3'-$NH_2$ oligonucleotide. This reaction is shown in FIG. 3.

Synthesis of N-(fluorescein-5'-thiocarbamoyl)diaminohexane

Figure 4:
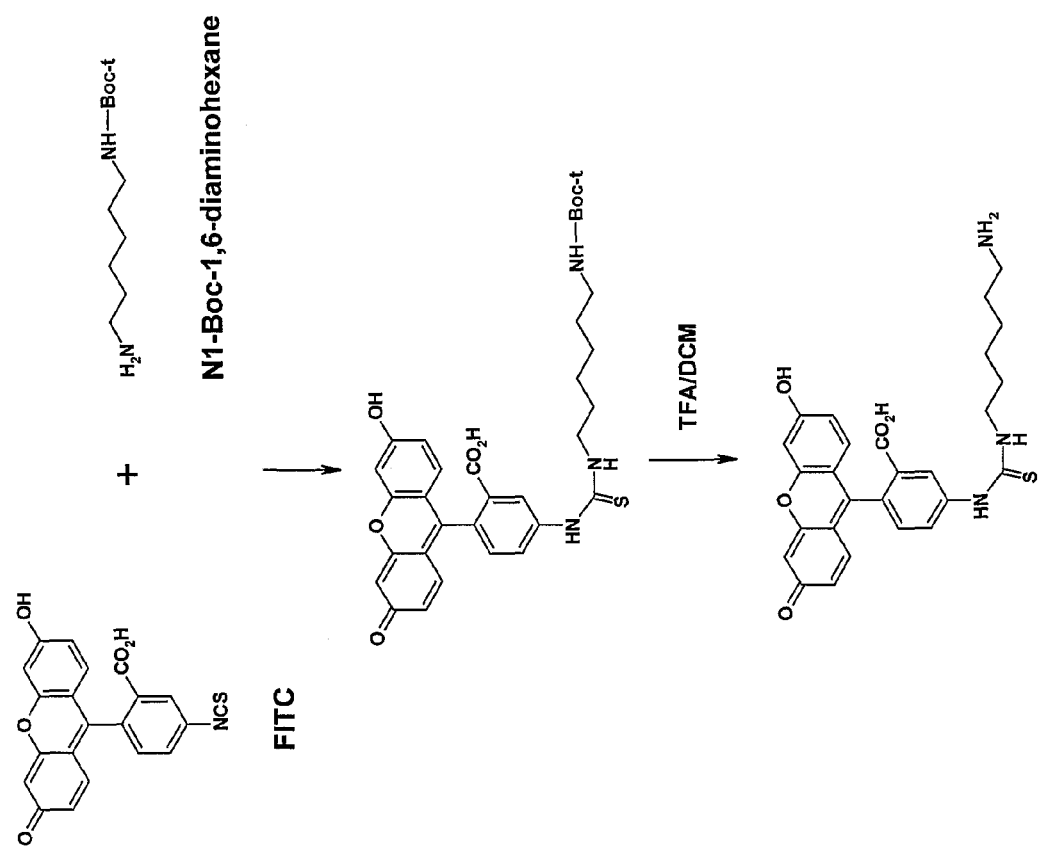
FIG. 4 is a diagram illustrating the synthesis N-(fluorescein-5'-thiocarbamoyl)diaminohexane.

Fluorescein isothiocyanate isomer I (90 mg) (FITC, minimum 98%, 0.23 mmol) was dissolved in 3 ml DMF, and 76 mg of $N_1$—Boc-1,6-diaminohexane hydrochloride (0.3 mmol) were added. The coupling reaction was started by dropwise addition of 0.6 mmol of triethylamine. The reaction mixture was incubated for 2 h at room temperature, and the volume was reduced by evaporation under reduced pressure (final volume approximately 0.5 ml). Cold water (5 ml) was added to the remaining mixture and acidified with 1 N HCl. The precipitate was collected by centrifugation, washed three times with cold water followed by centrifugation, until no trace of $N_1$-Boc-1,6-diaminohexane could be detected in the supernatant as determined by TLC and ninhydrin test. The final product was dried over $P_2O_5$. This synthesis is illustrated in FIG. 4.

To remove the Boc protecting group, the dried product was dissolved in 3 ml of dichloromethane (DCM), and the temperature was lowered with an ice bath. Two ml TFA were added to the solution which was then stirred for 30 min on ice. The reaction was followed by TLC. Fluorescent spots were visible under UV light. The solvent was evaporated under reduced pressure, and the waxy product was dissolved in acetone and precipitated by the addition of diethylether. For purification, the product was dissolved in 3 ml of DCM/ethanol (3:2, v/v) containing 4 ml of acetic acid in 100 ml mixture and passed through a 2 cm×12 cm $SiO_2$ column equilibrated with the same solvent. The product was pure by TLC. The Rf-values were 0.95 for FITC, 0.98 for $N_1$-(fluorescein-5'-thiocarbamoyl)-$N_6$—BOC-1,6-diaminohexane, and 0.64 for N-(fluorescein-5'-thiocarbamoyl)diaminohexane.

Synthesis of N,N'-bis-(3-maleimidopropionyl)poly(ethylene Glycol)

0.5 g of NH2-PEG3400-$NH_2$ (0.147 mmol) dissolved in 3 mL of anhydrous DMF was added dropwise to (3-maleimidopropionic acid NHS ester) (106 mg, 0.4 mmol) dissolved in 5 ml of anhydrous DMF with vigorous stirring at room temperature. The completeness of the reaction was confirmed by TLC and a negative ninhydrin test. After incubation for 2 h at room temperature, the solvent was removed by rotary evaporation at room temperature under reduced pressure. The product was dissolved in 2 ml of buffer A (0.1 M sodium phosphate, 0.15 M NaCl, pH 7.2) containing 10 mM EDTA. Insoluble impurities were removed by centrifugation. The clear supernatant was passed over a Sephadex G-25 column pre-equilibrated with buffer A. The product was pure by TLC and ninhydrin test. The aqueous solution of the product was stored at −20° C.

Figure 5:
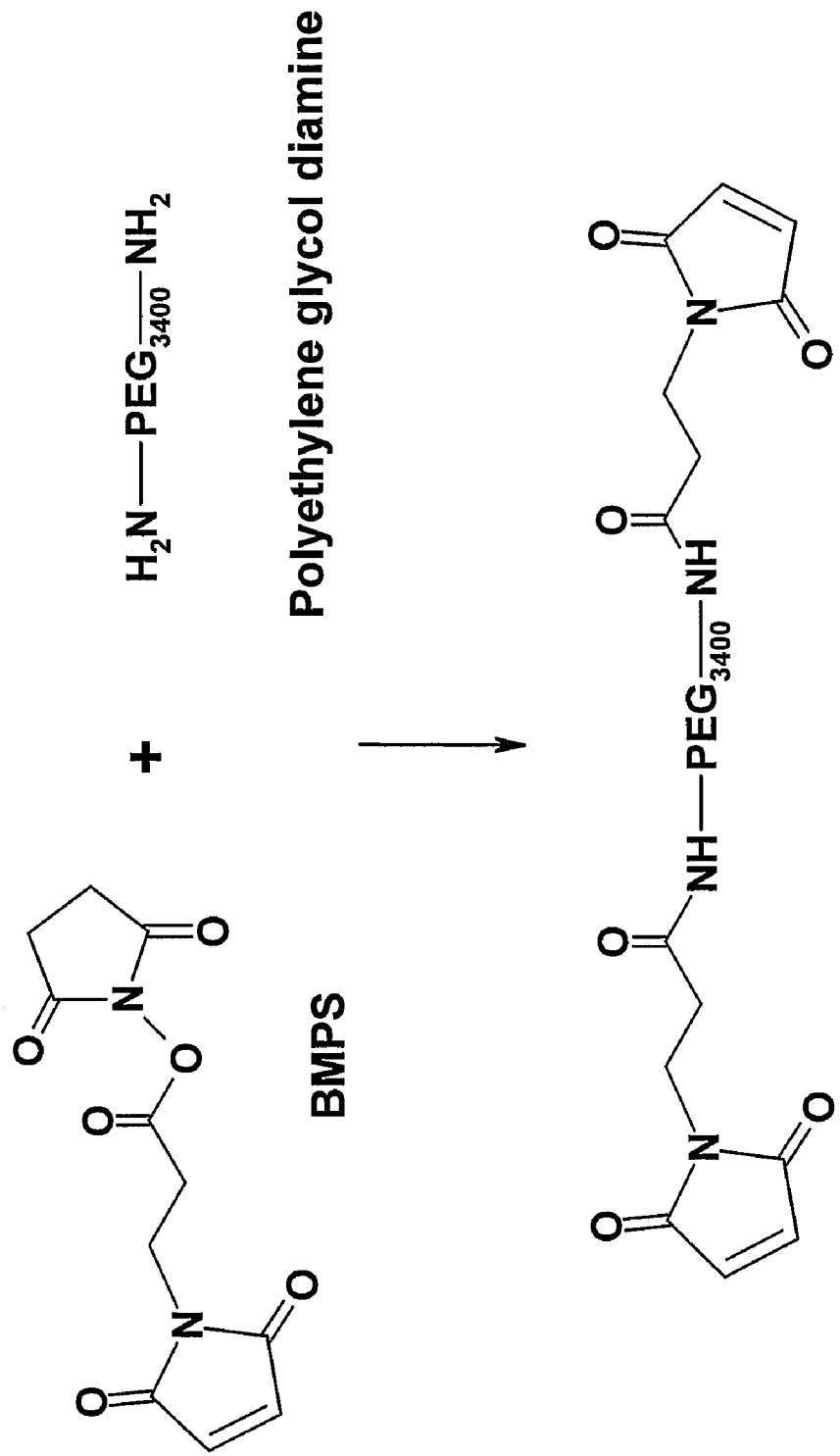
FIG. 5 is a diagram illustrating the synthesis N,N'-bis-(3-maleimidopropionyl)poly(ethylene glycol)

$^1$H-NMR spectra of the product dissolved in $(CD_3)_2SO$ indicated the following δ-values: 7.05 singlet 4H—HC═CH—, 3.74 triplet 2H N—CH2, 3.5 singlet hydrogens from PEG, 3.03 triplet 2H $CH_2$—CONH. The values were consistent with the product being the expected N,N'-bis-(3-maleimidopropionyl)poly(ethylene glycol) diamide. The content of maleimido groups was measured indirectly by a method relying on the reaction of —HC═CH— with the sulfhydryl of given amounts of 2-mercaptoethylamine (2-MEA) and the titration of unreacted sulfhydryl with 5,5'-dithiobis-2-nitrobenzoate (DTNB, Ellman's reagent) as follows. An appropriate amount of 2-MEA in water was added to the aqueous solution of N,N-bis-3-maleimidopropionyl)poly(ethylene glycol) diamide and incubated for 30 min at room temperature. DTNB (25 μL solution of 10 mg/mL in ethanol) was added and the absorbance at 412 nm read after 10 min incubation at room temperature. The absorbance was standardized with known amounts of 2-MEA, and the amount of unreacted sulfhydryl groups calculated. The content of maleimide groups in the sample of N,N'-bis-(3-maleimidopropionyl)poly(ethylene glycol) diamide was calculated by subtraction of the amount of unreacted 2-MEA from the initial amount of 2-MEA. From this value, the yield of the synthesis of N,N'-bis-(3-maleimidopropionyl)-poly(ethylene glycol) diamide was calculated to be 65%. This synthesis is shown in FIG. 5.

Introduction of Thiol Groups into Antibodies: Reduction of Intrinsic Disulfide Bonds with 2-mercaptoethylamine (2-MEA)

Mouse monoclonal antibody (mAB) against rat transferrin receptor CD71 (clone OX-26, isotype $IgG_{2a}$) was commercially obtained at a concentration of 1 mg/ml PBS containing 10 mM sodium azide. Mouse monoclonal antibody $IgG_{2a}κ$ (UPC 10, Sigma) in place of mAB OX-26 was used to generate a control conjugate and also a standard curve for protein measurements. The mAB OX26 solution was concentrated using a microcentrifuge membrane filter (Sigma Ultrafree-CL microcentrifuge filters, regenerated cellulose, cutoff 30 kDa) at 4° C. and 5000×g. The mAB storage buffer was changed to buffer A (0.1 M sodium phosphate, 0.15 M NaCl, pH 7.2) containing 10 mM EDTA. The concentration of the mAB was adjusted to 3-5 mg/ml. Mouse mAB UPC 10 was dissolved in buffer A to give the same concentration as mAB OX 26. Solid 2-mercaptoethylamine hydrochloride (2-MEA) (6 mg/ml) was stirred into the antibody solutions and the mixture incubated for 90 min at 37° C. The disulfide-reduced antibodies were purified by diafiltration with buffer A (degassed under $N_2$) using microcentrifuge membrane filters (regenerated cellulose, cut off. 30 kDa) at 4° C. and 5000×g. The step was performed until the diafiltrate was completely free of 2-MEA as measured spectrophotometrically at 412 nm after incubation with 5,5'-dithiobis(2-nitrobenzoic acid) (DTNB, Ellman's reagent). The number of thiol groups in the disulfide-reduced antibody solutions was calculated by reading the absorbance at 412 nm (e=14.15×10³ M⁻¹ cm⁻¹ at 25° C.) after 10 min incubation of 0.5 ml antibody solution with 25 µl of DTNB solution (10 mg/ml in ethanol) at pH 8.0. The antibody protein concentration was measured according to method of [65]. The results indicated that the disulfide-reduced antibodies contained 3.1-3.5 thiol groups per molecule of IgG-molecule. SEC-HPLC analysis showed only one peak of MW 150 kDa indicating that the reduced antibody had maintained its molecular integrity. The preparations were rather stable in the presence of EDTA even in the absence of reducing agent, and no significant losses in free thiol groups were observed overnight at 4° C.

Synthesis of mAB OX-26/N,N'-bis-(3-maleimidopropionyl)-PEG Diamide Conjugate Immediately after preparation, the solution of reduced antibody was added dropwise to the stirred aqueous solution of N,N'-bis-3-maleimidopropionyl)-PEG diamide (in 50-fold molar excess of maleimide groups over the thiol groups of the antibody) at room temperature. The reaction mixture was incubated for 2 h at room temperature, and the unreacted N,N'-bis-(3-maleimidopropionyl)-PEG diamide was removed by dialysis in buffer A (50 kD membrane, overnight with three times buffer change). The preparation of antibody-N,N'-bis-(3-maleimidopropionyl)-PEG diamide conjugate was used immediately for further synthetic reactions.

The completeness of the conjugation reaction was indicated by the results of SEC-HPLC. When measuring absorbance at 220 nm wavelength, the only material eluted was in the position of 7.20-7.26 min which represented the conjugate, while none eluted in the position of 13.4-13.7 min for the unreacted N,N'-bis-3-maleimidopropionyl)-PEG diamide. The content of maleimide groups in the antibody conjugate was determined indirectly using 2-MEA and Ellman's reagent as described above for the synthesis of N,N-bis-(3-maleimidopropionyl)-PEG diamide. The antibody protein concentration was determined according to method of [65]. The results indicated 3.0 maleimido groups per antibody molecule and were in agreement with the assumption that the free thiol groups of the disulfide-reduced antibodies preparations had fully reacted with N,N'-bis-(3-maleimidopropionyl)-PEG diamide. Moreover, because SEC-HPLC analysis showed only one peak of MW 150 kDa, products of crosslinking could be excluded.

Figure 6:
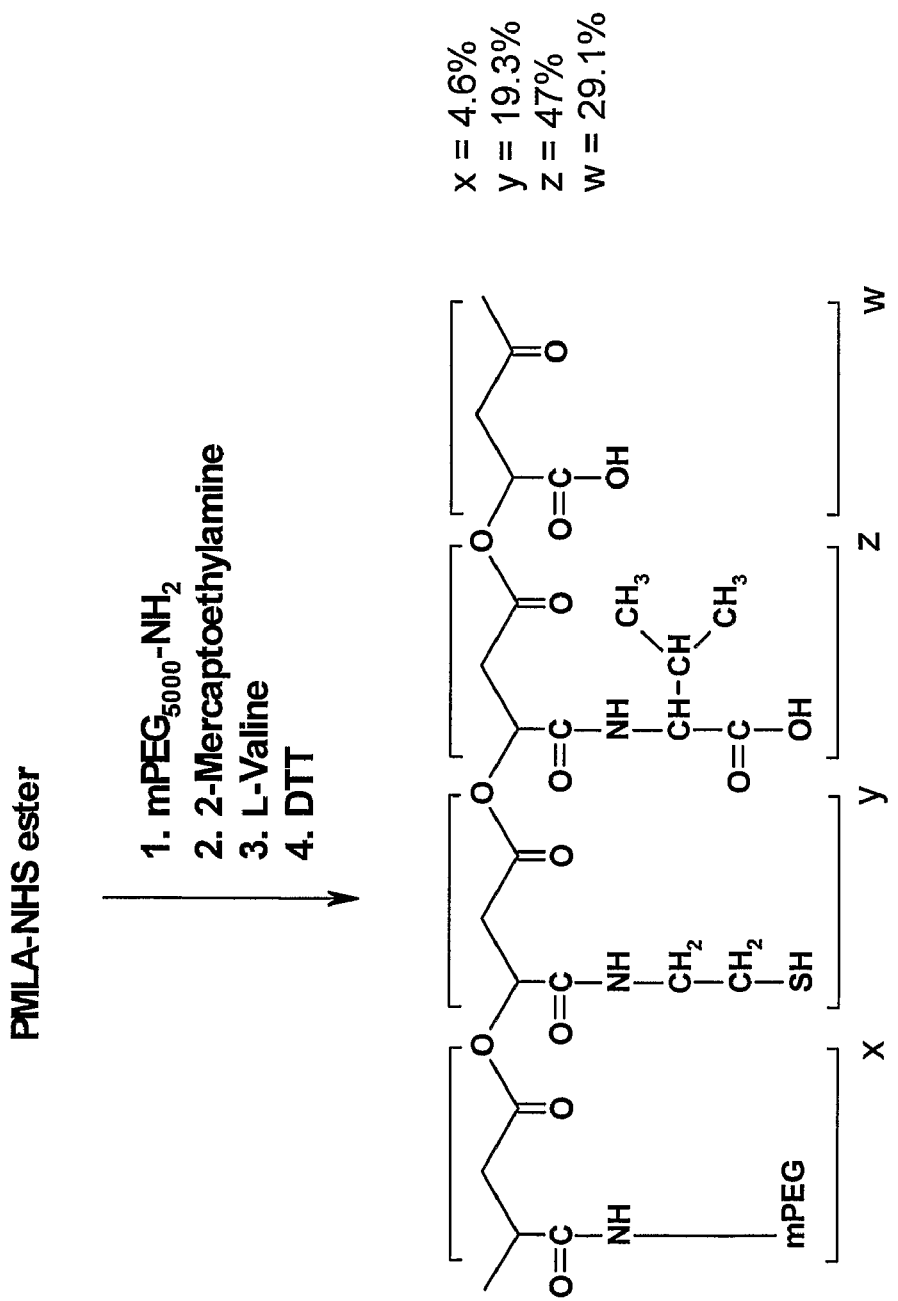
FIG. 6 is a diagram illustrating the synthesis of PMLA/L-valine/2-mercaptoethylamine/mPEG5000-NH2 conjugate

Synthesis of PMLA/L-valine/2-mercaptoethylamine/mPEG$_{5000}$-NH$_2$ Conjugate For the synthesis of PMLA/L-valine/2-mercaptoethylamine/mPEG-NH$_2$ conjugate, 1 mmol (with regard to malyl units) of PMLA-NHS ester (preparation P3: 85% NHS ester) was dissolved in 10 ml of anhydrous DMF. First, mPEG5000-NH2 (50 µmol in 2 mL DMF, corresponding to 5 mol-% of the NHS activated malyl units) and 200 µmol of N-ethylmorpholine were added in this sequence and the mixture stirred at room temperature for 30 min until the reaction was completed according to TLC with the ninhydrin test (negative versus positive ninhydrin reaction at origin). Next, 200 µmol of a 50 mM solution of 2-MEA in DMF (corresponding to 20 mol-% of NHS-activated malyl groups) and 200 µmol of N-ethylmorpholine were added to the reaction mixture with stirring for 30 min at room temperature. Again, the reaction was complete according to TLC (Rf=0.27 for 2-MEA and Rf=0 for the polymer conjugate) with the ninhydrin reaction. The synthesis is shown in FIG. 6.

According to the stoichiometry of the added reagents, 4.5% and 19.3% of the PMLA-NHS ester equivalents had been replaced by PEG and 2-MEA, respectively. The remaining unreacted NHS esters equivalents were allowed to conjugate to L-valine (1 mmol in 5 ml water), added dropwise in the presence of 0.1 g of NaHCO$_3$ (1.2 mmol). The reaction mixture was stirred for 1 h at room temperature and neutralized under cooling with 0.1 M HCl. The solvent was evaporated at 30° C. under reduced pressure. The dried product was dissolved in 10 ml of buffer A (0.1 M sodium phosphate, 0.15 M NaCl, pH 7.2) containing 10 mM EDTA and 1 ml of 0.5 M DTT. After 10 min at room temperature, the mixture was centrifuged at 20 000×g for 5 min and the clear supernatant passed over a Sephadex G25 column (2.5 cm×60 cm) pre-equilibrated with buffer A, and the product containing fractions lyophilized.

The composition of the PMLA/L-valine/2-mercaptoethylamine/mPEG-NH$_2$ conjugate was analyzed by $^1$H NMR and UV-VIS spectroscopy. The content of thiol groups was measured by the addition of 25 µl of DTNB solution (10 mg/ml in ethanol) to 1 mg of lyophilized conjugate dissolved in 1 ml of sodium phosphate buffer (pH 8.0, 100 mM) and reading the absorbance at 412 nm wavelength after 30 min incubation at room temperature. In case of the preparation of PMLA/L-valine/2-mercaptoethylamine/mPEG-NH2/FITC conjugate (see below), the reaction mixture was also diafiltrated with a microcentrifuge membrane filter (regenerated cellulose, cut off 5 kDa) at 5000×g before reading the 412 nm absorbance. The Ellman method for assaying thiols is based on the reaction of thiols with the chromogenic DTNB (5,5'-dithiobis-2-nitrobenzoate, FW 396.4) whereby formation of the yellow 5-thio-2-nitrobenzoic acid (TNB) is measured.

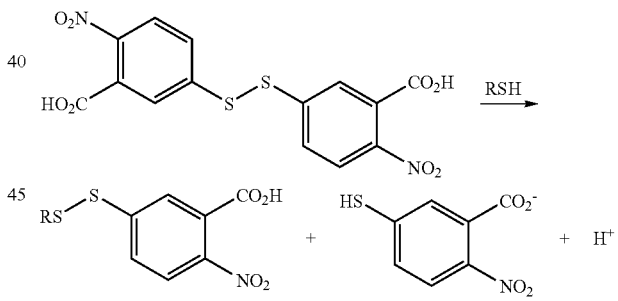

The reason for filtration in case of FITC-conjugate is to separate TNB from FITC-conjugate because the presence of fluorescence makes the detection of TNB impossible. During the filtration TNB passes the membrane, FITC-conjugates are retained, and the absorbance of the filtrate is measured (The filtration is not for removal of free dye. The free dye is already removed before this reaction).

The sulfhydryl content was calculated with regard to 2-MEA standards. The content of L-valyl moieties was determined by quantifying the free amino groups after total hydrolysis using the trinitrobenzenesulfonic acid (TNBS) assay and RP-HPLC as follows: 1 mg of the conjugate and 30-50 µL of 6 N HCl were placed in a 100 µL capillary tube. The sealed capillary was incubated in an oven at 100° C. for 12 to 16 hrs. After hydrolysis the contents were transferred into an Eppendorf tube (rinsing the capillary tube with water to be quantitative) and evaporated to complete dryness by gentle warming. This material was redissolved in water and centrifuged. A 10-30 μl aliquot of the supernatant was added to 300 μl of sodium bicarbonate buffer (0.4 g $NaHCO_3$ in 10 ml water, pH 8.5). After addition of 150 μL of 0.1% (w/v) TNBS aqueous solution, the mixture was incubated for 30 min at 37° C. After centrifugation, 20 μL of the reaction mixture were separated by RP-HPLC using a linear gradient of 30 min (0-10 min, 100% water, 10-40 min from 0-60% acetonitrile). The content of valyl moieties was calculated on the basis of the 340 nm absorbance in the eluent with regard to known amounts of L-valine as standards. The molar ratio of mPEG:valine: 2-MEA of the conjugate was determined by $^1H$ NMR.

Synthesis of PMLA/mAB OX-26/morpholino antisense oligonucleotide/L-valine/2-mercaptoethylamine/mPEG-$NH_2$ Conjugate Freshly prepared mAB OX-26-PEG-maleimide was added dropwise to PMLA/L-valine/2-mercaptoethylamine/mPEG-$NH_2$ conjugate at 4° C. with stirring. A 100 molar excess of free thiol groups (conjugate) over maleimido groups was applied, allowing all antibodies to become conjugated with the polymer. After 30 nm in of incubation, the reaction was complete. The completeness of the reaction was confirmed by SEC-HPLC. The PMLA/mAB OX-26/L-valine/2-mercaptoethylamine/mPEG-$NH_2$ conjugate was purified by diafiltration in buffer A using microcentrifuge membrane filters (regenerated cellulose, MW cut off of 100 kDa) at 4° C. and 5000×g. The mAb-containing PMLA conjugate was retained by the filter and only protein-free PMLA/L-valine/2-mercaptoethylamine/mPEG-$NH_2$ conjugate passed through the filter. The diafiltration was repeated until no trace of the protein-free polymer conjugate was detected in the diafiltrate as confirmed with SEC-HPLC.

The protein content of the PMLA/mAB OX-26/L-valine/2-mercaptoethylamine/mPEG-$NH_2$ conjugate was measured by the method of [66]. The same amount of unconjugated mAb showed an approximately 10% higher absorbance, and thus, the measured protein content was corrected by factor of 0.9. (This factor was empirically derived from the fact that, although no antibody was found to leak through the diafiltration, the retained (conjugated) antibody amounted to only 90% of the educt antibody.) The reason for this discrepancy is not known. The concentration of the remaining free thiol groups of the protein-containing conjugate was determined as described above. It was found that approximately 70% of the initial thiol groups were still present. The concentration of the protein-containing conjugate was adjusted to 3 mM with regard to thiol groups.

In the next step, 5 μmol of PDP-morpholino antisense oligonucleotides for α4 and β1 chains of laminin 8 (5 ml of the 1 mM solution of PDP-morpholino antisense oligonucleotides) was added dropwise with stirring to the purified solution of the PMLA/mAB OX-26/L-valine/2-mercaptoethylamine/mPEG-NH2 conjugate equaling a concentration of 15 μmol of free thiol groups (5 ml of 3 mM solution of the protein-containing conjugate). The molar ratio of antisense α4 chain to the antisense β1 chain was 1:1. The reaction mixture was incubated overnight at 4° C. The completeness of the reaction was confirmed by SEC-HPLC indicating a single peak in the eluent with 260 nm absorbance and the absence of absorbance in the positions of free PDP-morpholino antisense oligonucleotides. The obtained PMLA/mAB OX-26/morpholino antisense oligonucleotide/L-valine/2-mercaptoethylamine/mPEG-$NH_2$ conjugate was purified by diafiltration using microcentrifuge membrane filter (regenerated cellulose, cut off: 100 kDa) at 4° C. and 5000×g centrifugation. The content of the free sulfhydryl groups at this stage was determined with Ellman's reagent at 412 nm. The content of antisense morpholino oligonucleotides was measured by absorbance at 260 nm after reduction of the disulfide groups with 50 mM DTT for 2 h at 37° C. and separation by SEC-HPLC. Specifically, the 260 nm light absorbing peaks were compared with those obtained for reduced PDP-morpholino antisense oligonucleotides as standards.

Figure 7:
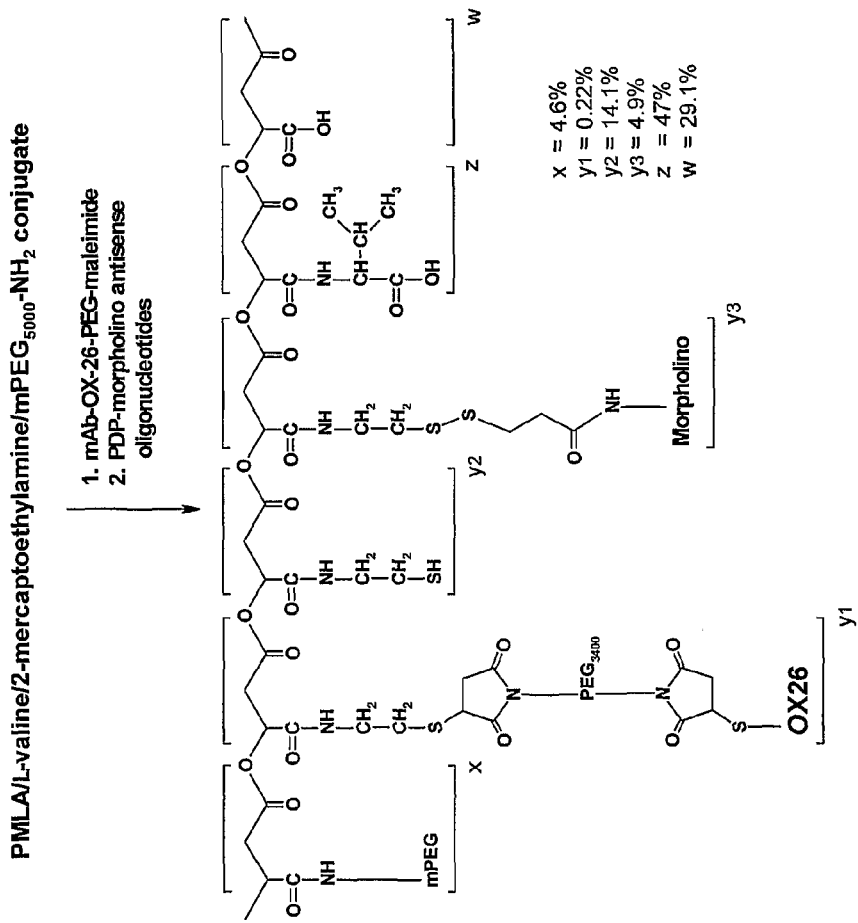
FIG. 7 is a diagram illustrating the synthesis of PMLA/mAB OX-26/morpholino antisense oligonucleotide/L-valine/2-mercaptoethylamine/mPEG5000-NH2 conjugate

The protein content of the PMLA/mAB OX-26/morpholino antisense oligonucleotide/L-valine/2-mercaptoethylamine/mPEG-NH2 conjugate was measured by the method of [65]. The molar ratio of antibody: morpholino antisense oligonucleotide varied from 1:20 to 1:26 resulting a y1-value of 0.19%-0.25% (see FIG. 7 for overall synthesis). Free sulfhydryl groups were blocked with N-ethylmaleimide, and unreacted reagent was removed by diafiltration as above.

Figure 8:
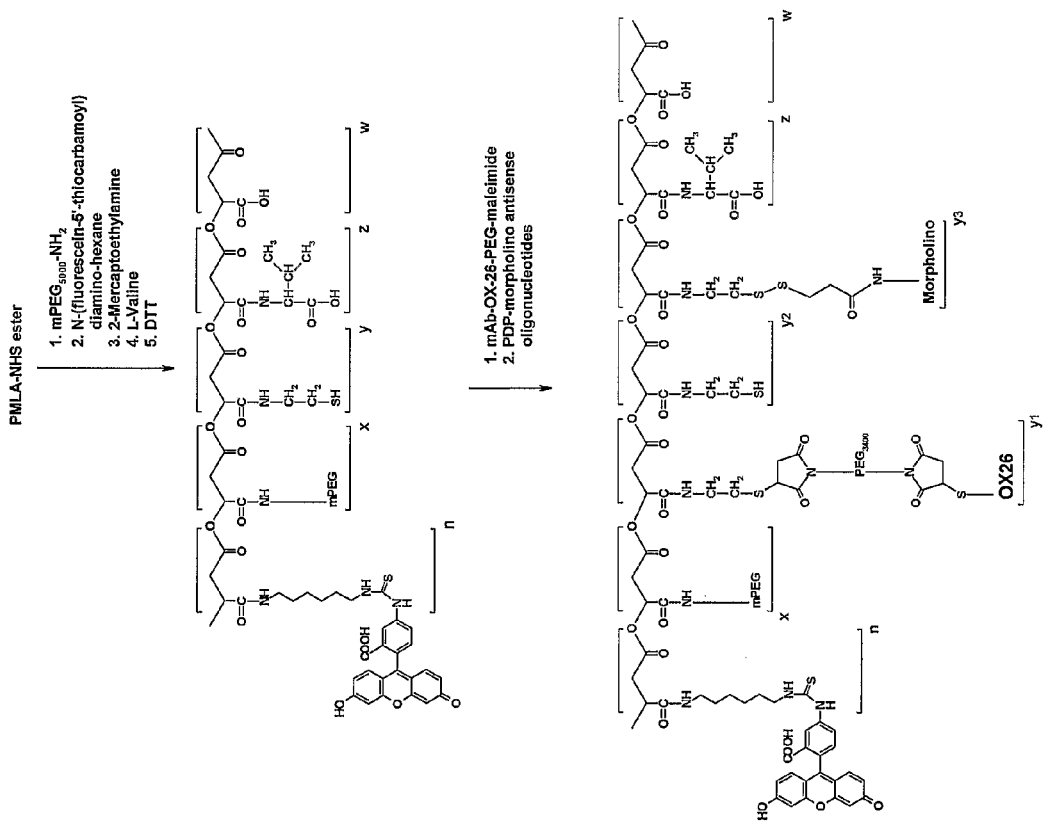
FIG. 8 is a diagram illustrating the conjugation of FITC to PMLA/mAB OX-26/morpholino antisense oligonucleotide/L-valine/2-mercaptoethylamine/mPEG-NH2 conjugate.

Conjugation of FITC to PMLA/mAB OX-26/morpholino Antisense Oligonucleotide/L-valine/2-mercaptoethylamine/mPEG-NH2 Conjugate For detection under biological conditions, PMLA/mAB OX-26/morpholino antisense oligonucleotide/L-valine/2-mercaptoethylamine/mPEG-NH2 conjugate was covalently labeled with fluorecein isothiocyanate (FITC). This label was, however, introduced after conjugation of mPEG-$NH_2$ to PMLA-NHS esters indicated above. The solution of N-(fluorescein-5'-thiocarbamoyl)diamino-hexane was prepared in a mixture of DMF and PBS (1:1) to a final concentration of 25 mM. To the solution of mPEG-$NH_2$/PMLA conjugate (1 mmol with regard to malyl units of PMLA-NHS ester, preparation P3: 85% NHS ester) 25 μmol of N-fluorescein-5'-thiocarbamoyl)diamino-hexane (n=2.5% in FIG. 7) and 100 μmol of N-ethylmorpholine were added, and the mixture was incubated at room temperature for 30 min. The reaction was followed by TLC. After completion of the reaction, fluorescence was detected only at the origin. The construction of the FITC to PMLA/mAB OX-26/morpholino antisense oligonucleotide/L-valine/2-mercaptoethylamine/mPEG-$NH_2$ conjugate then followed the same route as described above in the absence of the dye. The content of FITC in the conjugates was measured by absorption of the FITC-moiety at 490 nm. FITC-carrying conjugates were also detected by a Merek-Hitach fluorescence detector with the excitation wavelength set to 447 nm and the emission wavelength set to 514 nm. The content of FITC was calculated by comparing the absorbance or fluorescence of samples with that of standard samples generated by quantitative conjugation of varying amount of FITC to carrier polymer as described above. The conjugate was used directly for cell culture experiments. This synthesis is shown in FIG. 8.

Hemolysis Assay. FIG. 9 shows the membrane disruptive activity of the polymers as measured using a red blood cell (RBC) hemolysis assay. The fresh human RBCs were isolated by centrifugation of whole human blood at 2000 g for 5 min. The RBCs were washed three times with cold 100 mM sodium phosphate buffer of the desired pH (pH 5.85 or pH 5.5). The final pellet was resuspended in the same buffer to give a solution with 108 RBCs per 1 ml. The polymers were dissolved in 100 mM dibasic sodium phosphate buffer at the desired pH at a concentration of 10 mg/ml. The polymer concentration was 2.5 nmol/$10^8$ RBCs. Hemolysis in distilled water was used to produce 100% lysis. RBCs in buffer with no polymer was used as reference controls. The hemolysis assay was performed by adding the polymer solution to the suspended RBCs in 1 ml of the appropriate buffer. The RBCs were mixed by inverting the tube several times, and incubated for 1 h in a 37° C. water bath. After incubation, the RBCs were centrifuged for 10 nm in at 13,500×g to sediment intact cells and the lysis was determined by measuring the absorbance of the supernatants at 541 nm which reflects the amount of hemoglobin released by the RBCs. The relative increase 100 $(A-A_o)/A_{total}$ in absorbance at 541 nm wavelength of the cell-free supernatant was measured as an indicator of membrane rupture. The results show that PMLA-PEG-Valine, PMLA-PEG-Valine-AS, and PMLA-PEG-Valine-AS-mAB infer membrane destabilization in contrast to PMLA-PEG which stabilizes RBC membranes. Comparison shows that destabilization is due to the presence of PMLA-conjugated valine. At decreasing pH (simulating maturation of endosomes to become lysosomes), the carboxyl groups of valine become protonated, and destabilization increases due to an increased lipophilicity of the charge-neutralized valine moieties.

Figure 10B:
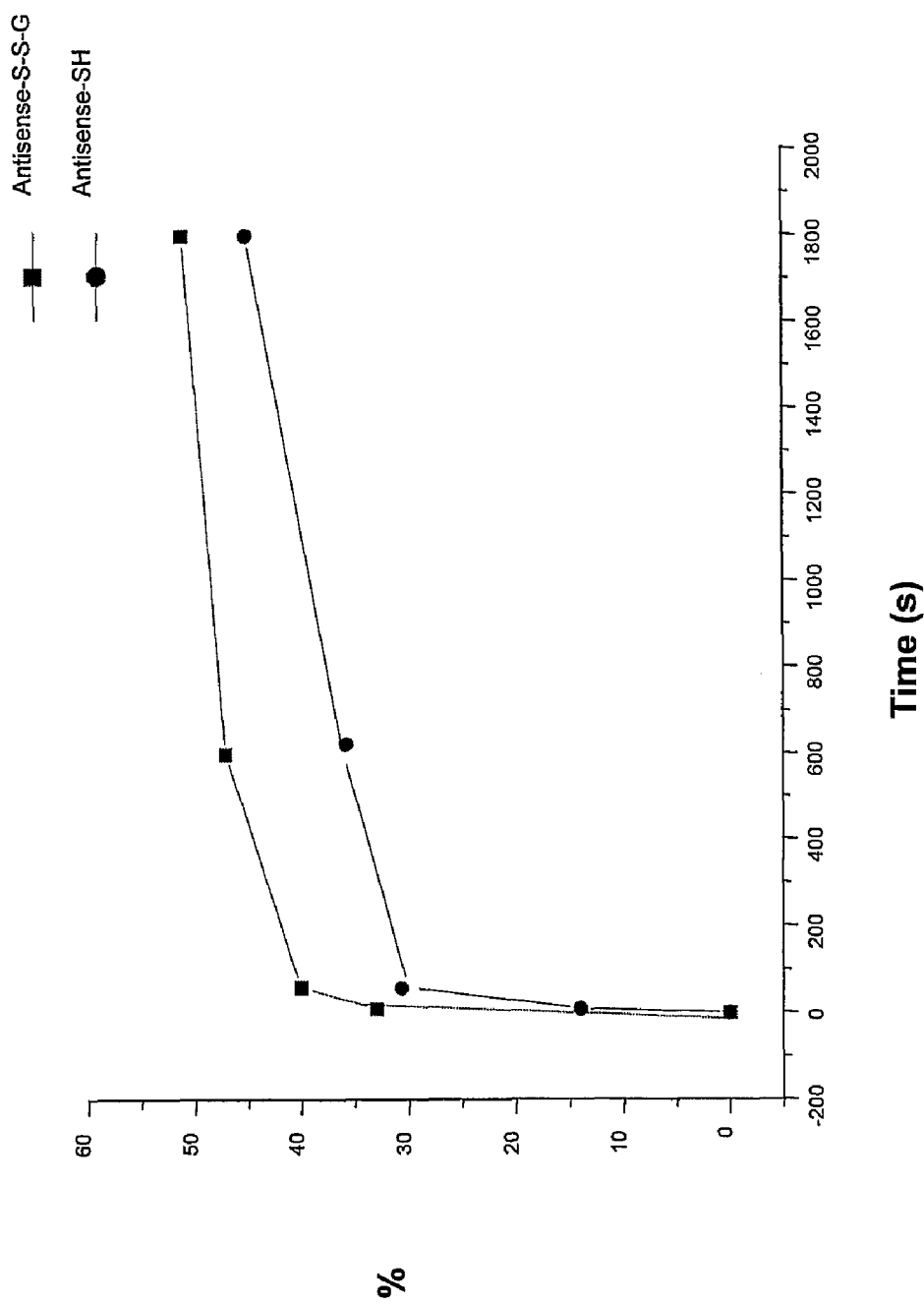
FIG. 10b shows the percentage of oligo release over time in response to f reduction with glutathione.

Release of the Morpholino Oligos. FIGS. 10a and 10b shows the release of morpholino antisense oligonucleotides from the drug carrier due to the cleavage of the disulfide bond by glutathion (glutathion-SH). The cleavage of the disulfide bond is a two-step reaction. In the first step, one equivalent of glutathion-SH reacts with the disulfide forming a mixed disulfide antisense oligonucleotide —S—S-glutathion (striped columns) (FIG. 10a) and one equivalent of free antisense oligonucleotide-SH (solid columns). Over time the mixed disulfide decreases and the free antisense increases. This reaction is rapid as is seen in FIG. 10b. In the second step, the mixed disulfide reacts with a second equivalent of glutathion to yield the disulfide glutathion-S—S-glutathion and free antisense oligonucleotide-SH. This second reaction is slow. The two-step mechanism and the relative rates of the reactions are typical for this so called disulfide exchange reaction. The results show that the oligonucleotides are very efficiently cleaved from the drug carrier in the cytoplasm, which contains glutathion at this given concentration.

To mimic cytoplasmic release of antisense morpholino oligonucleotides from the drug vehicle as shown in the figures, 5 mM GSH (γ-L-glutamyl-L-cysteinylglycine, MW 307.33) was added to the reaction mixture at room temperature. The mixture contained 0.25 mM of the drug vehicle in water. At various times, the reaction was stopped by the addition of an excess of N-ethylmaleimide (20 mM final concentration) over total sulfhydryl moieties. The reduced antisense was detected as N-ethylmaleimidyl antisense. The reaction products were separated by HPLC and the released antisense morpholinos were detected by their UV absorbance at 260 nm. The results are shown in FIG. 10b. A Complete (100%) release is referenced to the reduction in the presence of 50 mM DTT at 37° C. for 1 h. HPLC analysis was performed with a Merck-Hitach analytical HPLC unit using a gel filtration column. Separation was carried out on a (300×7.7 mm) Macherey & Nagel 125-5 GFC-HPLC column using sodium phosphate buffer (50 mM, pH 7.4) with a flow rate of 0.75 ml/min.

Treatment of Human Glioblastoma Grown in Brain of Nude Rat with Laminin-8 Antisense Oligonucleotides Conjugated to Poly-L-Malic Acid Specific drug delivery is crucial for treating tumors and reducing side effects for normal cells. Simultaneous inhibition of several molecular targets at the level of protein synthesis may be highly effective in preventing tumor growth and progression. Laminin-8 chains overexpression is associated with glioma progression, and laminin-8 blocking inhibits glioma invasion in vitro [34].

Methods

Polymalic acid (PMLA). A multifunctional drug delivery construct consists of modules attached to the pendant carboxyl groups of polymalic acid (PMLA). The polymer is a natural product of *Physarum polycephalum* [27]. The modules are (1) morpholino antisense oligonucleotides conjugated to the scaffold by disulfide bonds, which bonds are cleaved in the cytoplasm to release the free drug, (2) antibodies against transferrin receptor for cancer cell targeting and receptor-mediated endocytosis, (3) short chain PEG-conjugated L-leucine and directly coupled L-valine, both linked through amide bonds, to provide pH-dependent lipophilicity to disrupt endosomal membranes, (4) long chain PEG for increasing time in circulation, and (5) fluorescent reporter molecules (fluorescein, Cy5 or similar fluorophores) to detect the construct molecule within the tissue/cell.

Scheme of Drugs used for the animal treatment.
Drug 1: antisense oligo to laminin α4+ antisense oligo to laminin β1 (α4:β1=1:1);
Drug 2: antisense oligo to laminin α4+ antisense oligo to laminin β1 (α4:β1=1:1)+monoclonal anti-transferrin receptor antibody (antibody OX-26 to rat CD71 from Chemicon International) as vehicle for delivery to the fast dividing cells [35, 36, 37, and 38];
Drug 3: antisense oligo to laminin α4+ antisense oligo to laminin β1+antisense oligo to EGFR (α4:β1:EGFR=1:1:1);
Drug 4: antisense oligo to laminin α4+ antisense oligo to laminin β1+ antisense oligo to EGFR (α4:β1:EGFR=1:1:1)+anti-transferrin receptor antibody.
Drugs 1A, 2A, 3A and 4A were identical to the drugs of the corresponding number (i.e., Drug 1 was identical to Drug 1A) except that the corresponding sense oligos were used in place of the antisense oligos.

Drug 1: antisense oligo nucleotide to laminin α4 chain and antisense oligo nucleotide to laminin β1 chain conjugated to PMLA; Drug 2: antisense oligo nucleotide to laminin α4, antisense oligo nucleotide to laminin β1, and monoclonal anti-transferrin receptor antibody (antibody OX-26 from Chemicon International) conjugated to PMLA. Controls (Drugs 1A and 2A) were the same carrier conjugates with the antisense oligos replaced by corresponding sense oligos. The human U-87MG glioblastoma cell line was used for in vitro experiments and injected intracranially into NIHRNU-M NIH nude outbred homozygous rats (Taconic Inc.).

NIH Nude outbred rats (Tac:N:NIH-Whn, Taconic) were used for these tests. For antisense treatment, we used Morpholino oligos (Gene Tools, LLC) as the most specific, stable and effective both in vitro and in vivo. Morpholinos have been used in the past successfully for in vitro studies, but in vivo, their delivery has been less successful [6,7]. Poly-L-malic acid (PMLA) was used as a delivery carrier for getting the Morpholinos into the cells. The principle of the method for purification of PMLA has been described [25]. A modern scaled-up PMLA production method [27] was used. The chemistry of PMLA functional groups has been investigated [28, 29], showing that the chemical derivatization and purification of the products in both organic and aqueous solvents is readily achievable. For our experiments, PMLA was chemically conjugated to a monoclonal antibody against transferrin receptor, to make the drug most specific for fast dividing cells [35, 36, 37, and 38], in addition to targeting tumor-specific laminin-8 chains.

Preliminary toxicity studies were performed for morpholino oligonucleotides, PMLA and their conjugate after complete synthesis. 30 days after injection of each chemical, gross and micro-pathological analysis were performed, and no abnormal changes were noted. Animals did not develop neurological abnormalities and their appetites were also normal. Animal test subjects were created by injecting human glioblastoma U-87MG cells intracranially using a stereotactic device. The drug treatments started three days after the injection of tumor cells.

For intracranial treatment, rats were injected with antisense oligos on days 3, 7, 10 and 14 (four treatments total) as diagrammed below.

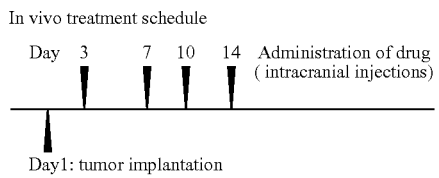

Groups of 12 rats each were injected with oligos to laminin-8 α4+β1 chains at doses of 0.5 mg/kg or 2.5 mg/kg. Control groups of 11 rats each were injected with sense oligos to α4 chain+β1 chain at 0.5 mg/kg or at 2.5 mg/kg. All surgical and non-surgical procedures were performed according IACUC protocol 001118, dated August of 2003. For intracarotid treatment, a group of rats had a catheter implanted into the carotid artery right after the tumor implantation. The catheter was connected to an implantable subcutaneous injection port. The rats were given infusion of 900 μl of antisense and sense oligos solution (0.06 ml per minute for 15 minutes with a peristaltic pump) into the right carotid artery via the subcutaneous port chamber followed by heparin flush. Rats were euthanized in 30 minutes after the end of infusion. The control consisted of: (a) 3 rats that were euthanized on day without any kind of treatment to obtain normal control tissue, and (b) 4 rats with tumors that were sham-injected intracranially with PBS on days 1, 3, 7, 10 and 14, and euthanized for tissue harvest as soon as they developed neurological symptoms caused by tumor progression.

Results

Figure 11:
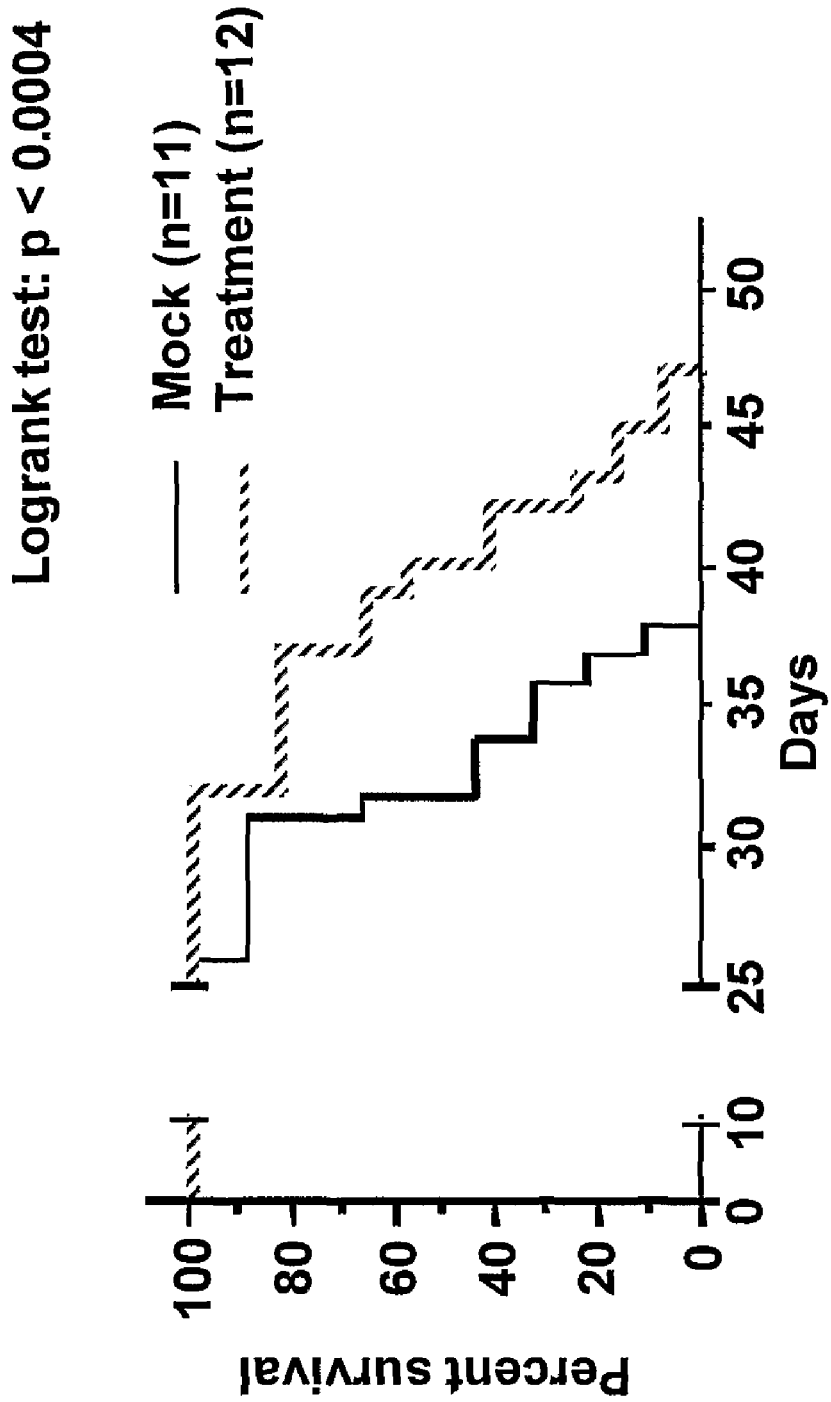
FIG. 11 shows a Kaplan-Meir survival curve of rats after treatments with Drug 2 compared to Drug 2A and/or PBS (mock) as analyzed by a log rank test with significance at $p<0.01$.

Intracranial tumor treatment. Drug 2 doses of 0.5 and 2.5 mg/kg were equal for the treatment in the survival study. After intracranial administration of four doses of Drug 2, the animal survival time was increased by 30%, p<0.008 (FIG. 11), compared to rats treated with PBS (mock) or sense oligos (Drug 2A). Two treatments, however, only produced a marginal effect. Drug 1 without transferrin receptor antibody did not affect survival. Therefore, the mechanism of drug cell delivery is probably transferrin receptor-mediated endocytosis. Interestingly, addition of antisense to EGFR to Drug 2 (Drug 4) resulted in loss of activity, possibly due to increased glioma cell survival in hypoxic conditions with EGFR inhibited [39].

Figure 12:
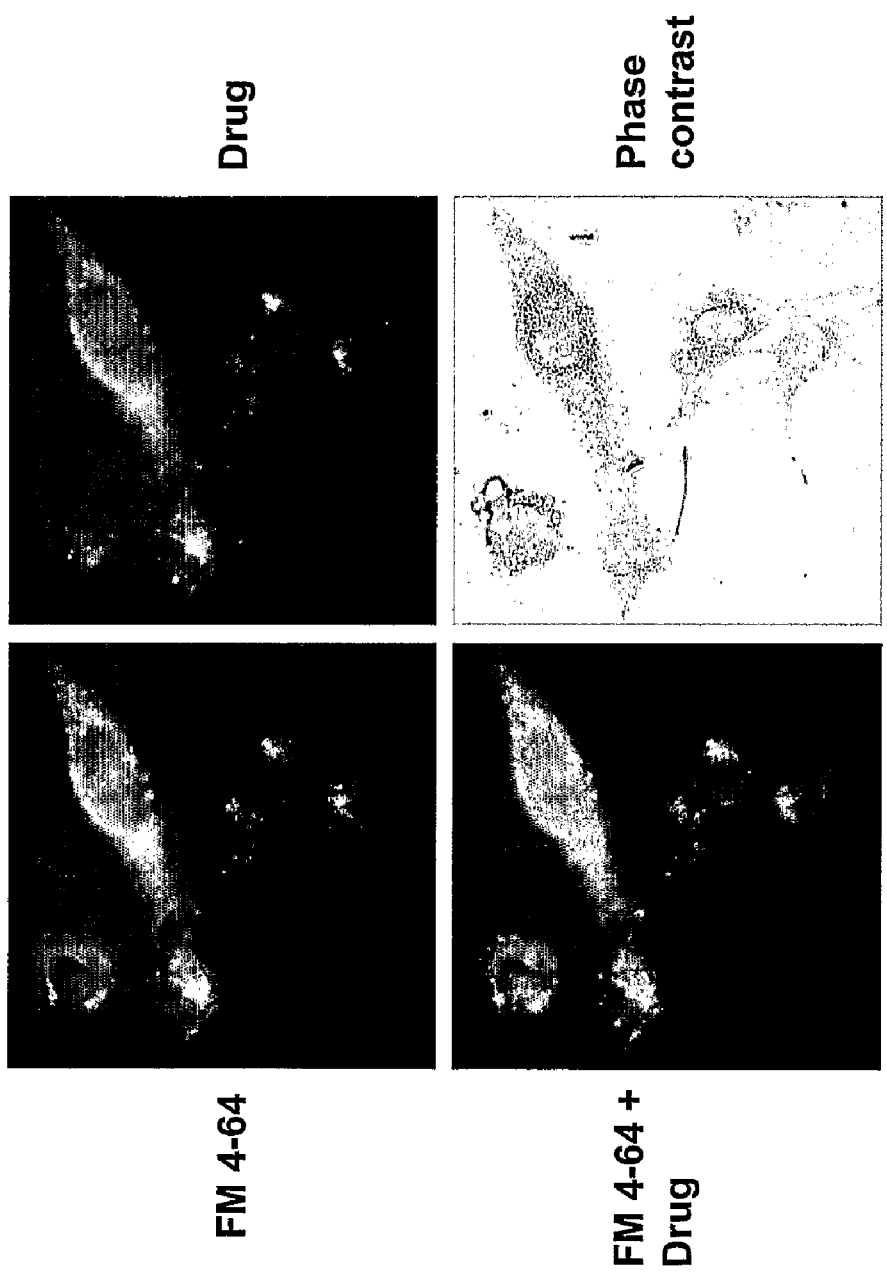
FIG. 12 is Co-distribution of endosomal marker FM 4-64 with Drug 2 (30 min) in cultured glioma U-87MG cells. By confocal microscopy, FM 4-64 is seen in the cytoplasmic endosomes (upper left), and Drug 2 is found in the same place (upper right). Both labels co-localize (lower left, yellow color)

The mechanism of drug internalization was investigated in cultured glioma cells. When cells were treated with fluorescein-labeled Drug 2 and rhodamine-labeled endosomal marker FM 4-64 (Molecular Probes, Eugene, Oreg.) the staining for both compounds showed co-localization. In 10 minutes, stains co-localized near cell membrane and in 30 minutes both labels were found in the endosomes (FIG. 12).

If cells were pretreated with transferrin receptor antibody and then treated with Drug 2 in ten minutes, the drug was not seen in the cytoplasm (data not shown). These results suggest that transferrin receptor antibody is required as part of the active drug because it allows drug penetration into cells by receptor-mediated endocytosis, after which the antisense oligos can be released within the target cells. If the cells are pretreated with free antibody to transferrin, the receptors are blocked and the antibody on the drug is unable to bind.

We found that Drug 2 decreases vessel density and specific laminin chain expression in human gliomas xenotransplanted to nude rats. We demonstrated that Drug 2 designed to inhibit laminin-8 expression reduces vessel density in tumors. These vessels were visualized by immunostaining for von Willebrand factor. The number of vessels was counted in both drug-treated and untreated animals, in five microscopic fields on three serial sections (15 fields per tumor) under ×200 magnification, using a Zeiss Axioscop microscope connected to an image capturing system (Hamamatsu, Japan). The data were input into NIH ImageJ software to quantify the vessels. Statistical significance was determined by ANOVA.

Figure 13:
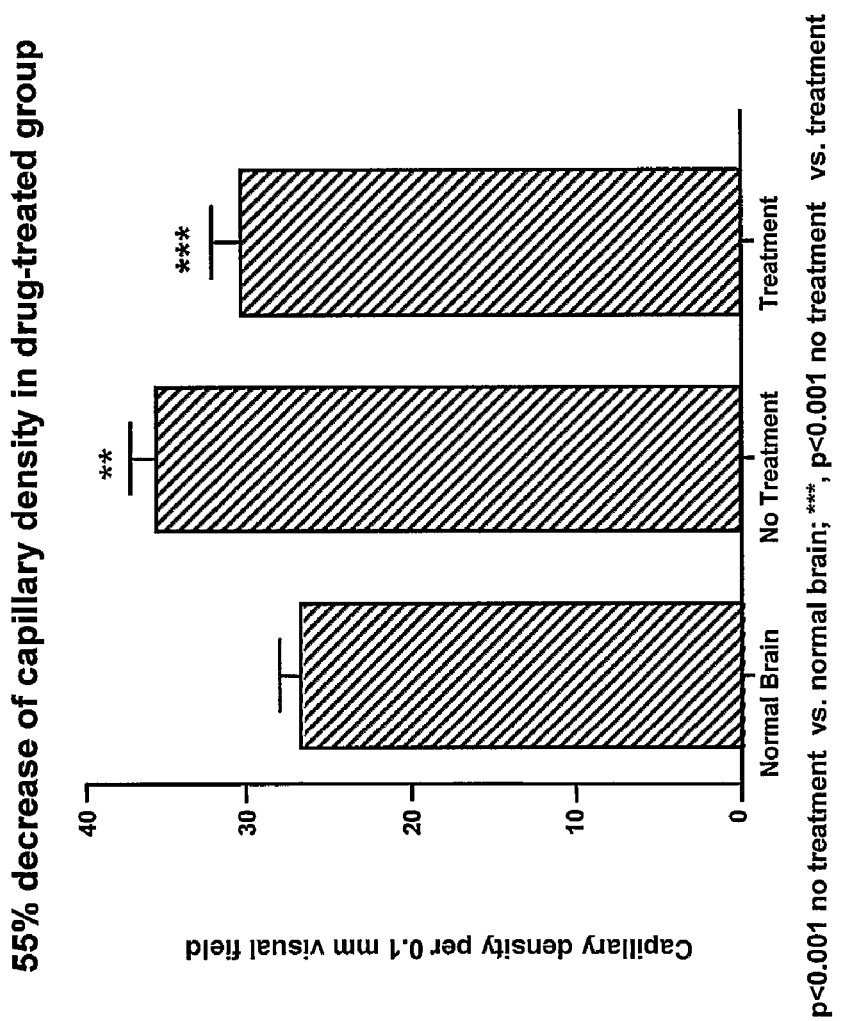
FIG. 13 is a chart illustrating that vessel density is increased in tumors compared to normal brain and that Drug 2 reduces tumor vessel density by 55%.

Angiogenesis. As shown on FIG. 13, microvascular density in the U87MG human tumors without treatment was significantly higher than in normal brain. After four intracranial treatments with Drug 2 tumor vessel density was reduced by 55%. Data are presented for control brains of three sham-operated (normal) rats (45 microscopic fields), five rats (75 microscopic fields) with untreated tumors, and five rats with Drug 2-treated tumors (75 microscopic fields). The results confirm the antiangiogenic mechanism of action of Drug 2 designed to inhibit laminin-8 expression.

Figure 14:
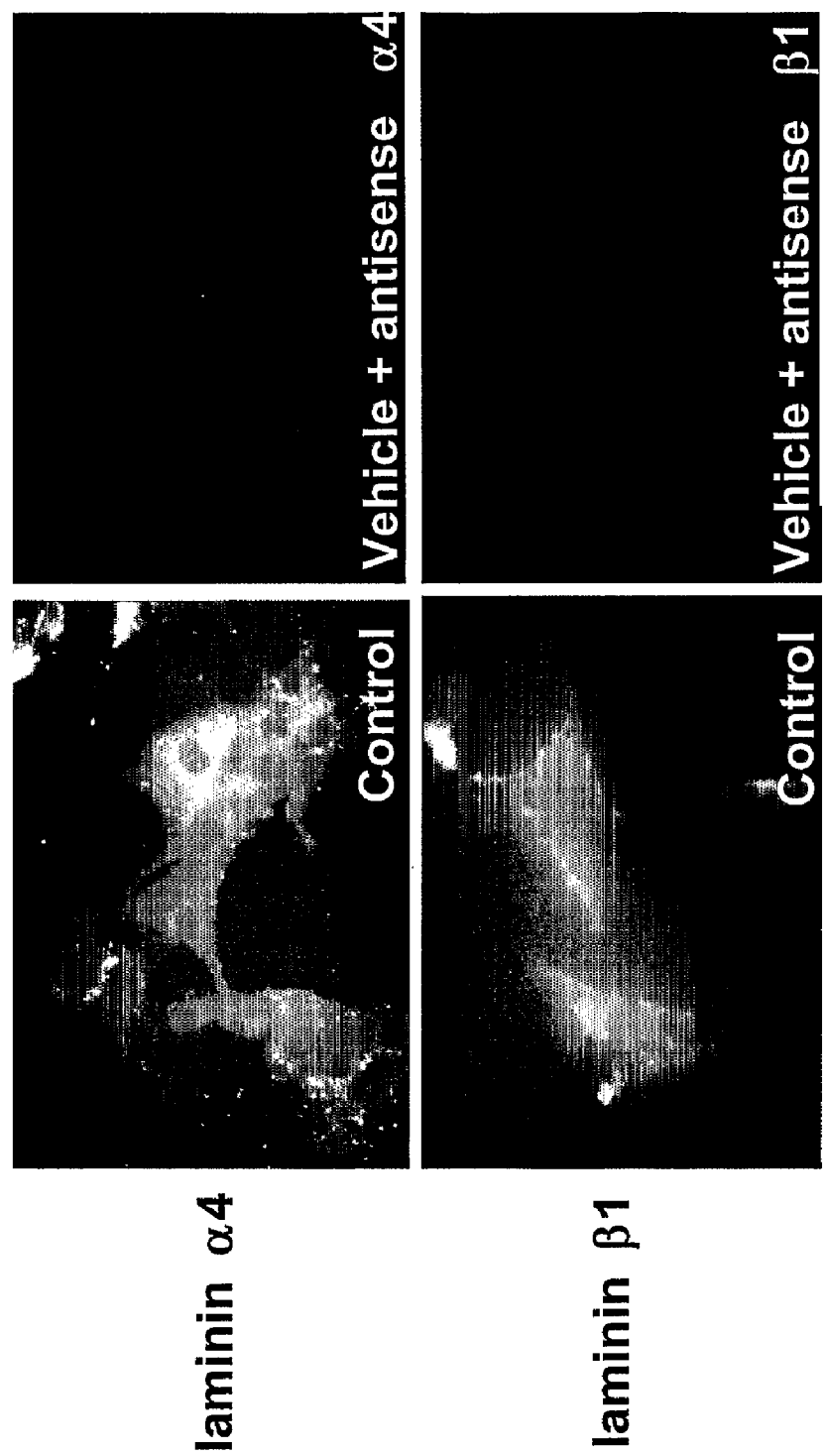
FIG. 14 shows immunofluorescence staining of U87MG glioma cultures for laminin chains. PMLA vehicle-conjugated antisense oligos (Drug 2) inhibit laminin expression ($\alpha 4$ is red and $\beta 1$ is green). Nuclei are counterstained with DAPI (blue)
Figure 15:
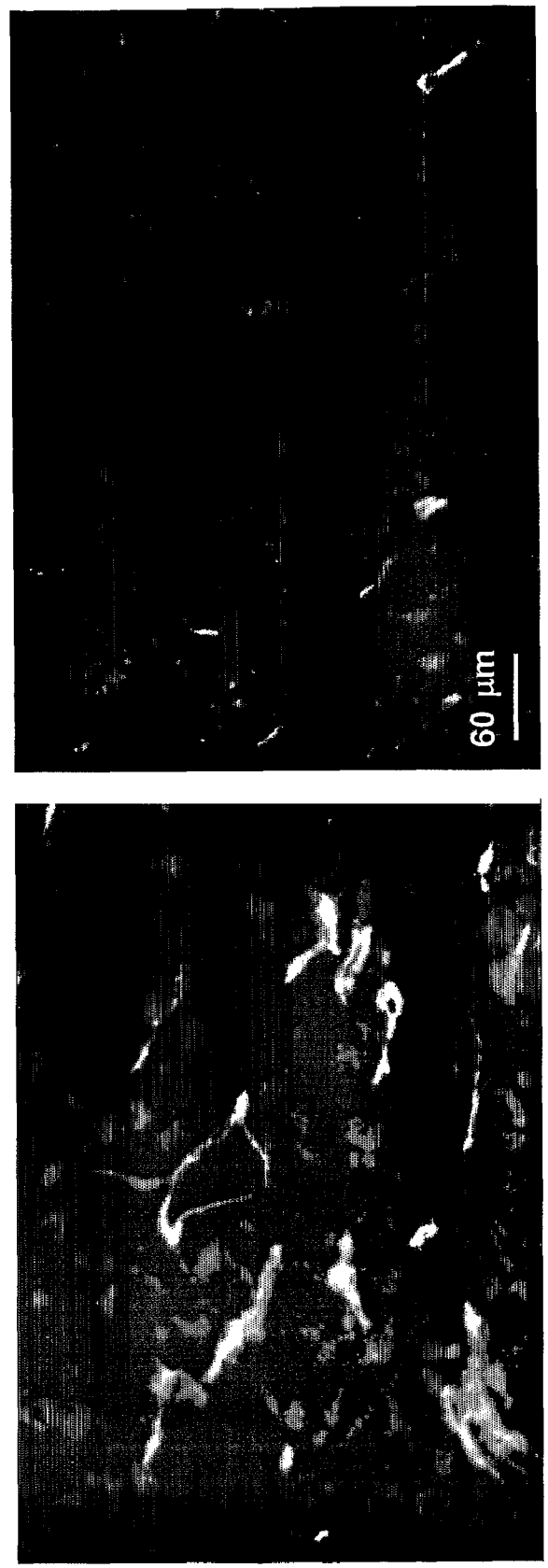
FIG. 15 shows immunofluorescence analysis of xenotransplanted tumors using a monoclonal antibody to human laminin $\beta 1$ chain; laminin $\beta 1$ chain synthesis was inhibited in GBM after Drug 2 administration.

Laminin chain immunostaining. It was important to show that Drug 2 in fact inhibited the expression of targeted laminin-8 chains. To this end, experiments were conducted both in vivo and in vitro. For tumor immunostaining, an antibody to human laminin-8 β1 chain was used that does not recognize rat laminin but reacts with tumor-derived laminin. FIG. 14 shows the effect in cell culture where the antisense effectively eliminates the immunostaining. As shown in FIG. 15, Drug 2 also effectively reduced immunostaining for laminin β1 chain in xenotransplanted human tumors.

Figure 16:
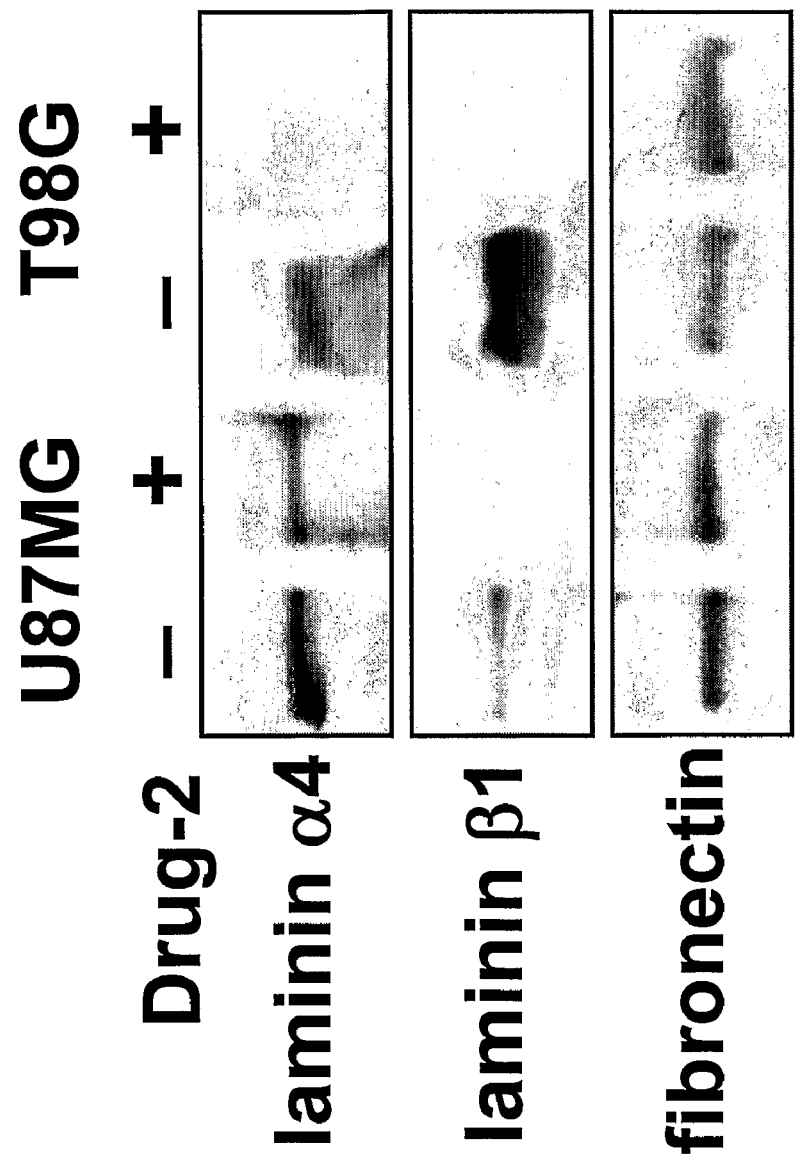
FIG. 16 shows western blot analysis of inhibition of laminin-8 chain expression in two glioblastoma multiforma (GBM) cell cultures, U87MG and T98G: −, no treatment, +, treatment with Drug 2.

Inhibition of laminin-8 expression in vitro was assessed in conditioned media of two cultured human gliomas, U87MG and T98G, treated for 3 days with Drug 2 Western blot analysis on FIG. 16 shows marked reduction of laminin α4 chain (three-fold decrease by densitometry) and disappearance of laminin β1 chain. Therefore, Drug 2 efficiently inhibits the expression of target laminin chains both in vivo and in vitro.

Intracarotid and Intravenous Tumor Treatment In Vivo

Fourteen days after human U87-MG glioma cells inoculation into rat brain for intracarotid treatment, Group of 3 rats had a catheter implanted into the carotid artery right after the tumor implantation. The catheter was connected to an implantable subcutaneous injection port. The rats were given infusion of 900 pt of antisense and sense oligos solution (0.06 ml per minute for 15 minutes with a peristaltic pump) into the right carotid artery via the subcutaneous port chamber followed by heparin flush. Drug 2 was injected at a concentration of 2.5 μg/kg for intracarotid treatment or via the tail vein at a concentration of 5 μg/kg (3 rats as well). The drug distribution was examined at 1, 3, 12 and 24 hours after injection. Using the fluorescence unit, we detected the drug in transplanted tumor cells (heavy staining) and vascular cells (lighter staining) of the brain (FIG. 17). Drug 2 was visualized by means of a rhodamine stained antibody that labels (in red) the transferrin antibody carried by Drug 2. The cell nuclei are counterstained with DAPI (blue). Rat brain (right panel) shows limited, mainly vascular, staining while the transplanted U87MG tumor cells (left panel) are heavily labeled. Maximum concentration in these locations was achieved in 3 and 12 hours time-point after drug injection. These results confirm that Drug 2 penetrates the blood-brain barrier (BBB), possibly by means of receptor-mediated endocytosis.

Conclusions. An in vivo model has been developed that is suitable for studying laminin-8 expression and its inhibition in human tumors. The combination of antisense oligos to laminin-8 α4 and βchains (blockage of laminin-8) combined with a novel drug delivery vehicle, PMLA, efficiently inhibited laminin-8 expression in a xenografted intracranial human glioma in rats. After a preliminary four-times antisense treatment, the survival of treated animals with glioma was significantly increased, with p<0.008. These data indicate that PMLA-based antisense drugs using laminin-8 as a therapeutic target are effective in inhibiting human brain tumors.

The following claims are thus to be understood to include what is specifically illustrated and described above, what is conceptually equivalent; what can be obviously substituted and also what essentially incorporates the essential idea of the invention. Those skilled in the art will appreciate that various adaptations and modifications of the just described preferred embodiment can be configured without departing from the scope of the invention. The illustrated embodiment has been set forth only for the purposes of example and that should not be taken as limiting the invention. Therefore, it is to be understood that; within the scope of the appended claims, the invention may be practiced other than as specifically described herein.

REFERENCES

1. Astriab-Fisher A, Sergueev D S, Fisher M, Shaw B R, Juliano R L. Antisense inhibition of P-glycoprotein expression using peptide-oligonucleotide conjugates. Biochem Pharmacol, 60:83-90, 2000.
2. Komata T, Kondo Y, Koga S, Ko S C, Chung L W, Kondo S. Combination therapy of malignant glioma cells with 2-5A-antisense telomerase RNA and recombinant adenovirus p53. Gene Ther, 7:2071-2079, 2000.
3. Andrews D W, Resnicoff M, Flanders A E, Kenyon L, Curtis M, Merli G, Baserga R, Iliakis G, Aiken R D. Results of a pilot study involving the use of an antisense oligodeoxynucleotide directed against the insulin-like growth factor type I receptor in malignant astrocytomas. J Clin Oncol, 19:2189-2200, 2001.
4. Jansen B, Wacheck V, Heere-Ress E, Schlagbauer-Wadl H, Hoeller C, Lucas T, Hoermann M, Hollenstein U, Wolff K, Pehamberger H. Chemosensitisation of malignant melanoma by BCL2 antisense therapy. Lancet, 356:1728-1733, 2000.
5. Nielsen P E. Peptide nucleic acid targeting of double-stranded DNA. Methods Enzymol, 340:329-340, 2001.
6. Summerton J, Weller D. Morpholino antisense oligomers: Design, preparation and properties. Antisense Nucleic Acid Drug Dev, 7:187-195, 1997.
7. Lacerra G, Sierakowska H, Carestia C, Fucharoen S, Summerton J, Weller D, Kole R. Restoration of hemoglobin A synthesis in erythroid cells from peripheral blood of thalassemic patients. Proc Natl Acad Sci USA, 97:9591-9596, 2000.
8. Taylor M F, Paulauskis J D, Weller D D, Kobzik L. Comparison of efficacy of antisense oligomers directed toward TNF-α in helper T and macrophage cell lines. Cytokine, 9:672-681, 1997.
9. Arora V, Knapp D C, Smith B L, Statdfield M L, Stein D A, Reddy M T, Weller D D, Iversen P L. c-Myc antisense limits rat liver regeneration and indicates role for c-myc in regulating cytochrome P-450 3A activity. 3 Pharmacol Exp Ther, 292:921-928, 2000.
10. Shi N, Boado R J, Pardridge W M. Antisense imaging of gene expression in the brain in vivo. Proc Natl Acad Sci USA, 97:14709-14714, 2000.
11. Boado R J, Kazantsev A, Apostol B L, Thompson L M, Pardridge W M. Antisense-mediated down-regulation of the human huntingtin gene. J Pharmacol Exp Ther, 295:239-243, 2000.
12. Tanabe K, Kim R, Inoue H, Emi M, Uchida Y, Toge T. Antisense Bcl-2 and HER-2 oligonucleotide treatment of breast cancer cells enhances their sensitivity to anticancer drugs. Int J Oncol, 22:875-81, 2003.
13. Cho Y S, Cho-Chung Y S. Antisense protein kinase A RIalpha acts synergistically with hydroxycamptothecin to inhibit growth and induce apoptosis in human cancer cells: molecular basis for combinatorial therapy. Clin Cancer Res, 9:1171-1178, 2003.
14. Tortora G, Caputo R, Damiano V, Caputo R, Troiani T, Veneziani B M, De Placido S, Bianco A R, Zangemeister-Wittke U, Ciardiello F. Combined targeted inhibition of bcl-2, bcl-XL, epidermal growth factor receptor, and protein kinase A type I causes potent antitumor, apoptotic, and antiangiogenic activity. Clin Cancer Res, 9:866-871, 2003.
15. Jiang Z, Zheng X, Rich K M. Down-regulation of bcl-2 and bcl-XL expression with bispecific antisense treatment in glioblastoma in vitro induce to enhance caspase-dependent cell death. J Neurochem, 84:273-281, 2003.
16. Mycek M J, Harvey R A, Champe, P C. Pharmacology. Lippincott-Raven, 2nd ed., 1997 Philadelphia, N.Y. pp. 475.
17. Park J W. "Liposome-based drug delivery in breast cancer treatment." Breast Cancer Res.; 4:95-99 (2002).
18. Matsukado K, Sugita K Black K L. Intracarotid low dose bradykinin infusion selectively increases tumor permeability through activation of bradykinin B2 receptors in malignant gliomas. Brain Res, 792:10-15, 1998.
19. Ningaraj N S, Rao M K, Black K L. Adenosine 5'-triphosphate-sensitive potassium channel-mediated blood-brain tumor barrier permeability increase in a rat brain tumor model. Cancer Res, 63:8899-8911, 2003.
20. Torchilin V P, Lukyanov A N. "Peptide and protein drug delivery to and into tumors: challenges and solutions." Drug Discov Today; 8:259-66, 2003.
21. Peterson C M, Shiah J., Sun Y, Kopeckova P, Minko T, Straight R C, Kopecek J "HPMA copolymer delivery of chemotherapy and photodynamic therapy in ovarian cancer." Adv Exp Med Biol.; 519:101-23, 2003.
22. Maeda H, Fang J., Inutsuka T, Kitamoto Y. "Vascular permeability enhancement in solid tumor: various factors, mechanisms involved and its implications." Int Immunopharmacol.; 3:319-28, 2003.
23. Satchi-Fainaro R, Puder M, Davies J W, Tran H T, Sampson D A, Greene A K, Corfas G, Folkman J. Targeting angiogenesis with a conjugate of HPMA copolymer and TNP-470. Nat Med, 10:255-261, 2004.
24. Fischer H, Erdmann S, Holler E. An unusual polyanion from *Physarum polycephalum* that inhibits homologous DNA polymerase α in vitro. Biochemistry, 28:5219-5226, 1989.

25. Lee B S, Holler E. Effects of culture conditions on β-poly (l-malate) production by *Physarum polycephalum*. Appl Microbiol Biotechnol, 51:647-652, 1999.
26. Korherr C, Roth M, Holler E. Poly(β-l-malate) hydrolase from plasmodia of *Physarum polycephalum*. Can J. Microbiol. 41 (Suppl. 1):192-199, 1995.
27. Lee B S, Vert M, Holler E. Water-soluble aliphatic polyesters: poly(malic acid)s, in: Biopolymers Vol 3a (Doi Y, Steinbüchel A, eds) pp 75-103, Wiley-VCH, New York 2002.
28. Gasslmaier B, Holler E. Specificity and direction of depolymerization of β-poly(l-malate) catalysed by polymalatase from *Physarum polycephalum*. Fluorescence labeling at the carboxy-terminus of β-poly(l-malate). Eur J Biochem, 250:308-314, 1997.
29. Gasslmaier B, Krell C M, Seebach D, Holler E. Synthetic substrates and inhibitors of β-poly(l-malate)-hydrolase (polymalatase). Eur J Biochem. 267:5101-5105, 2000.
30. Barbaud C, Renard E, Langlois V, Guérin Ph. Novel macromolecules and supr-molecular materials for drug delivery. Natural and artificial hydrolyzable polyesters with functionalized side chains for bioactive molecular encapsulation. J Controlled Release, 72:225-309, 2001.
31. Braud C, Bunel C, Vert M. Poly(β-malic acid): a new polymeric drug-carrier. Evidence for degradation in vitro. Polym Bull, 13:293-299, 1985.
32. Cammas S, Béar M-M, Moine L, Escalup R, Ponchel G, Kataoka K, Guerin Ph. Polymers of malic acid and 3-alkylmalic acid as synthetic PHAs in the design of biocompatible hydrolyzable devices. Int J Biol Macromol, 25:273-282, 1999.
33. Pichon C, Goncalves C, Midoux P. Histidine-rich peptides and polymers for nucleic acid delivery. Adv Drug Deliv Rev, 53:75-94, 2001.
34. Khazenzon N M, Ljubimov A V, Lakhter A J, Fujiwara H, Sekiguchi K, Sorokin L M, Virtanen I, Black K L, Ljubimova J Y. Antisense inhibition of laminin-8 expression reduces invasion of human gliomas in vitro. Mol Cancer Ther 2003, 2:985-994.
35. Boado R J, Tsukamoto H, Pardridge W M. Drug delivery of antisense molecules to the brain for treatment of Alzheimer's disease and cerebral AIDS. J Pharm Sci, 87: 1308-1315, 1998.
36. Shi N, Pardridge W M. Noninvasive gene targeting to the brain. Proc Natl Acad Sci, 97:7567-7572, 2000.
37. Kurihara A, Deguchi Y, Pardridge W M. Epidermal growth factor radiopharmaceuticals: 111In chelation, conjugation to a blood-brain barrier delivery vector via a biotin-polyethylene linker, pharmacokinetics, and in vivo imaging of experimental brain tumors. Bioconjugate Chem, 10:505-511, 1999.
38. Bickel U, Yoshikawa T, Pardridge W M. Delivery of peptides and proteins through the blood-brain barrier. Adv Drug Deliv Rev, 46:247-279, 2001.
39. Steinbach J P, Klumpp A, Wolburg H, Weller M. Inhibition of epidermal growth factor receptor signaling protects human malignant glioma cells from hypoxia-induced cell death. Cancer Res, 64:1575-1578, 2004.
40. Duncan, R 1999. Polymer conjugates for tumor targeting and intracytoplasmic delivery. The EPR effect as a common gateway? Research Focus 2:441-449.
41. Seymour, L W, Miyamoto, Y, Maeda, H, Brereton, K Strohalm, J, Ulbrich, K, Duncan, R 1995. Influence of molecular weight on passive tumor accumulation of a soluble macromolecular drug carrier. Eur. J. Cancer 31A: 766-770.
42. Kopecek, J., Kopeckova, P., Minko, T., Lu, Z. 2000. HPMA copolymer-anticancer drug conjugates: design, activity, and mechanism of action. Eur. J. Biopharm. 50: 61-81.
43. Vincenzi, V., Ferruti, P., Ford, J., Duncan, R. 2001. Synthesis and preliminary evaluation of novel functionalized poly(ethylene glycol)-block-poly(ester-carbonate) copolymers as biodegradable carriers. Macromolecular Bioscience 1: 164-169.
44. Environmental health criteria 191. Acrylic acid. United Nations Environmental Programme/International Labour Organisation/World Health Organisation. International Programme on Chemical Safety. http://www.inchem.org/documents/ehe/ehc/ehc191.htm.
45. Li, C. 2002a. Poly(L-glutamic acid)-anticancer drug conjugates. Advanced Drug Delivery. 54:695-713.
46. Gill, T. J., Kunz, H. W., Papermarker, D. S. 1967. Studies on synthetic polypeptide analogues. J. Biol. Chem. 242: 3306-3318.
47. Chiang, C.-H., Yeh, M,-K. 2003. Contribution of poly (amino acids) to advances in pharmaceutical biotechnology. Current Pharmaceut. Biotechnol. 4: 8-16.
48. Angerer, B., Holler, E. 1995. Large complexes of β-poly (L-malate) with DNA polymerase α, histones, and other proteins in nuclei of growing plasmodia of *Physarum polycephalum*. Biochemistry. 34: 14741-14751.
49. Abdellaoui, K, Boustta, M, Vert, M, Morjani, H, Manfait, M. 1998. Metabolite-derived artificial polymers designed for drug targeting, cell penetration and bioresorption. Eur. J. Pharmaceutical Sciences 6:61-73.
50. Ljubimova, J. Y., Lakhter, A. J., Loksh, A., Yong, W. H., Riedinger, M. S., Miner, J. H., Sorokin, L. M., Ljubimov, A. V., and Black K. L. (2001) Overexpression of α4 chain-containing laminins in human glial tumors identified by gene microarray analysis. Cancer Research 61, 5601.
51. Bulmus, V, Woodward, M, Lin, L, Murthy, N S P, Hoffman, A. 2003. A new pH-responsive and gluthathione-reactive, endosomal membrane-siruptive polymeric carrier for intracellular delivery of biomolecular drugs. J Controlled Release 93:105-120.
52. Saito, G, Swanson, J A, Lee, K-D. 2003. Drug delivery strategy utilizing conjugation via reversible disulfide linkages: role and site of cellular reducing activities. Advanced Drug Delivery Reviews 55:199-215.
53. Lee, J H, Engler, J A, Collawn, F, Moore, B A. 2001. Receptor mediated uptake of peptides that bind the human transferrin receptor. Eur. J. Biochem. 268:2004-2012.
54. Kovar, M K Strohalm, J, Ulbrich, J, Brihova, B. 2002. In vitro and in vivo effect of HPMA copolymer-bound doxorubicin targeted to transferrin receptor of B-cell lymphoma 38C13. J. Drug Targeting 10:23-30.
55. Broadwell, R D, Baker-Cairns, B J, Friden P. M., Oliver, C, Villegas, J C. 1996. Transcytosis of protein through the mammalian cerebral epithelium and endothelium. III Receptor-mediated transcytosis through the blood-brain-barrier of blood-borne transferrin and antibody against the transferrin receptor. Exp. Neurol. 142:47-65.
56. Friden, P M. 1996. Utilization of an endogenous cellular transport system for the delivery of therapeutics across the blood-brain barrier. J. Controlled Release 46:117-128.
57. van Gelder, W, Cleton-Soeteman, M I, Huijskes-Heins, M I E, van Run, P R W A, van Eijk, H G. 1997. Transcytosis of 6.6-nm gold-labeled transferrin: an unltrastructural study in cultured porcine blood-brain barrier endothelial cells. Brain Research 746:105-116.

58. Li, H, Qian, Z M. 2002b. Transferrin/Transferrin receptor-mediated drug delivery. Medical Research Reviews 22:225-250.
59. Lee, H J, Engelhardt, B, Lesley, J, Bickel, U, Pardridge, W M. 2000. Targeting rat anti-mouse transferrin receptor mAB through BBB in mouse. J. Pharmacol. Exp. Therapeut. 292:1048-1052.
60. Friden, P M, Walus, L R M G F, Taylor, M A, Malfroy, B, Starzyk, R M. 1991. Anti-transferrin receptor antibody and antibody-drug conjugates cross the blood-brain barrier. Proc. Natl. Acad. Sci. USA 88:4771-4775.
61. Zhang, Y, Zhang, Y, Bryant, J, Charles, A, Boado, R J, Pardridge, W M. 2004. Intravenous RNA interference gene therapy targeting the human epidermal growth factor receptor prolongs survival in intracranial brain cancer. Clinical Cancer Research 10:3667-3677.
62. Lackey, C A, Press, O W, Hoffman, A S S P S. 2002. A biomimetric pH-responsive polymer directs endosomal release and intracellular delivery of an endocytosed antibody complex. Bioconjugate Chem. 13:996-1001.
63. Arpicco, S, Dosio, F, Bolognesi, A, Lubelli, C, Brusa, P, Stella, B, Ceruti, M, Cattel, L. 2002. Novel poly(ethylene glycol) derivatives for preparation of ribosome-inactivating protein conjugates. Bioconjugate Chem. 13:757-765.
64. Maruyama, K, Takahashi, N, Kazuhiro, T, Nagaike, K, Iwatsuru, M. 1997. Immunoliposomes bearing polyethyleneglycol-coupled Fab' fragment show prolonged circulation time and high extravasation into targeted solid tumors. FEBS Letters 413:177-180.
65. Bradford, M. (1976). A rapid and sensitive method for the quantitation of microgram quantities of protein utilizing the principle of protein dye-binding. Anal. Biochem. 72, 248-254.
66. Johnson, J. F. (1985) Size-exclusion chromatography. Encyclopedia of polymer science and engineering, Vol. 3, 501-523.
67. Devlin, T. M. 1997. Textbook of Biochemistry with Clinical Correlations. pp. 28-29. Wiley & Sons, INC. New York, USA.
68. Foulon, C F, Bigner, D D, Zalutsky, M R. 1999. Preparation and characterization of anti-tenascin monoclonal antibody-streptavidin conjugates for pretargeting applications. Bioconjugate Chem. 10:867-876.
69. Iwata, H, Matsuda, S, Mitsuhashi, K, Itoh, E, Ikada, Y. 1998. A novel surgical glue composed of gelatin and N-hydroxysuccinimide activate poly(L-glutamic acid): Part 1. Synthesis of activated poly(L-glutamic acid) and its gelation with gelatin. Biomaterials 19:1869-1876.
70. Juszczak, L, Manjula, B, Bonaventura, C, Acharya, A, Friedman, J M. 2002. UV Resonance Raman study of b93-modified hemoglobin A: Chemical modifier-specific effects and added influences of attached poly(ethylene glycol) chains. Biochemistry 41:376-385.
71. Schnaible, V, Przybylski, M. 1999. Identification of fluorescein-5'-isothiocyanate-modification sites in proteins by electrospray-ionization mass spectroscopy. Bioconjugate Chem. 10:861-866.
72. Willner, D, Train, P A, Hofstaed, S J, King, H D, Lasch, D J, Braslawsky, G R, Greenfield, R S, Kaneko, T, Firestone, R A. 1993. (6-Maleimidocaproyl)hydrazone of Doxorubicin—a new derivative for the preparation of immunoconjugates of doxorubicin. Bioconjugate Chem. 1993:521-527.
73. Fournié Ph, Domurado D, Guérin Ph, Braud C, Vert M, Pontikis R. In vivo fate of repeat-unit-radiolabelled poly (β-malic acid), a potential drug carrier. J Bioactive Compatible Polymers 7: 113-129, 1992.
74. Roufai M B, Midoux P. Histidylated polylysine as DNA vector: Elevation of the imidazole protonation and reduced cellular uptake without change in the polyfection efficiency of serum stabilized negative polyplexes. Bioconjugate Chem, 12: 92-99, 2001.
75. Benns J M, Choi J S, Mahato R I, Park J S, Kim S W. pH-sensitive cationic polymer gene delivery vehicle: N-Ac-poly(L-hitidine)-graft-poly(L-lysine) comb shaped polymer. Bioconjugate Chem, 11:637-645, 2000.
76. Ulbrich K, Subr V, Strohalm J, Plocova D, Jelinkova M, Rihova B. Polymeric drugs based on conjugates of synthetic and natural macromolecules: I. Synthesis and physico-chemical characterisation. J Control Release, 64: 63-79, 2000.
77. Bartus R T, Elliott P J. Dean R L, Hayward N J, Nagle T L, Huff M R, Snodgrass P A, Blunt D G. Controlled modulation of BBB permeability using the bradykinin agonist RMP-7. Exp Neurol, 142: 14-28, 1996.
78. Howl J. Fluorescent and biotinylated probes for B2 bradykinin receptors: Agonist and antagonists. Peptides, 20: 515-518, 1999.
79. Campa M J, Kuan C T, O'Connor-McCourt M D, Bigner D D, Patz. Jr E F. Design of a novel small peptide targeted against a tumor-specific receptor. Biochem Biophys Res Commun, 275: 631-636, 2000.

We claim:

1. A drug delivery molecule comprising:
   a polymerized carboxylic acid molecular scaffold having a plurality of pendant free carboxylic acid groups;
   a plurality of biologically active molecular modules, wherein each module is covalently linked to a pendant carboxylic acid of the molecular scaffold, wherein said active molecular modules comprise: at least one targeting module for promoting cellular uptake by a target cell; and at least one pro-drug module for altering cellular metabolism of the target cell; wherein the targeting or the pro-drug active molecular module comprises a polypeptide and/or polynucleotide; and
   wherein the scaffold is a poly(β-L-malic acid) homopolymer.

2. The drug delivery molecule according to claim 1, wherein the pro-drug is selected to inhibit expression of tumor-specific proteins.

3. The drug delivery molecule according to claim 1, wherein the poly(β-L-malic acid) has a weight-averaged molecular weight (Mw) between 2,500 and 100,000.

4. The drug delivery molecule according to claim 3, wherein the poly(β-L-malic acid) has a weight-averaged molecular weight (Mw) of at least about 5,000.

5. The drug delivery molecule according to claim 1, wherein each molecule of the polymerized carboxylic acid molecular scaffold has at least about 50 pendant carboxylic acid groups.

6. The drug delivery molecule according to claim 1, wherein the plurality of molecular modules further includes a molecular module for promoting disruption of biomembranes.

7. The drug delivery molecule according to claim 6, wherein said molecular module for promoting disruption of biomembranes comprises a molecule having lipophilic characteristics and groups that are charged at physiologic pH and become uncharged at lysosomal pH thereby increasing lipophilicity of said molecular module.

8. The drug delivery molecule according to claim 1, wherein the plurality of active molecular modules further includes a molecular module for prolonging circulation of the drug delivery molecule.

9. The drug delivery molecule according to claim 8, wherein the molecular module for prolonging circulation of the drug delivery molecule comprises polyethylene glycol.

10. The drug delivery molecule according to claim 1, wherein the plurality of active molecular modules further includes a reporter module for determining cellular uptake of the drug delivery molecule.

11. The drug delivery molecule according to claim 10, wherein the reporter module comprises a fluorescent molecule.

12. The drug delivery molecule according to claim 1, wherein the targeting molecule is selected to promote penetration of the blood brain barrier.

13. The drug delivery molecule according to claim 1, wherein the pro-drug molecular module is linked to the polymerized carboxylic acid molecular scaffold by a cleavable linkage that is cleaved when the drug delivery molecule enters a cell.

14. The drug delivery molecule according to claim 13, wherein the cleavable linkage is a disulfide linkage.

15. The drug delivery molecule according to claim 1, wherein the pro-drug molecular module comprises an antisense molecule.

16. The drug delivery molecule according to claim 15, wherein the antisense molecule is a morpholino antisense molecule.

17. The drug delivery molecule according to claim 15, wherein the antisense molecule interferes with production of laminin-8.

18. The drug delivery molecule according to claim 17, wherein the antisense molecule interferes with production of laminin-8 by altering production of a laminin subunit selected from the group consisting of $\alpha 4$ laminin and $\beta 1$ laminin.

* * * * *